US011419768B2

(12) United States Patent
Cavanaugh, II et al.

(10) Patent No.: US 11,419,768 B2
(45) Date of Patent: Aug. 23, 2022

(54) REDUCED PRESSURE, COMPRESSION SYSTEMS AND APPARATUSES FOR USE ON JOINTS

(71) Applicant: KCI Licensing, Inc., San Antonio, TX (US)

(72) Inventors: Matthew Francis Cavanaugh, II, San Antonio, TX (US); Justin Alexander Long, Bournemouth (GB); Richard Marvin Kazala, Jr., San Antonio, TX (US); Eric Woodson Barta, Castle Hills, TX (US)

(73) Assignee: KCI Licensing, Inc., San Antonio, TX (US)

( * ) Notice: Subject to any disclaimer, the term of this patent is extended or adjusted under 35 U.S.C. 154(b) by 715 days.

(21) Appl. No.: 16/278,638

(22) Filed: Feb. 18, 2019

(65) Prior Publication Data
US 2019/0175414 A1 Jun. 13, 2019

Related U.S. Application Data

(60) Continuation of application No. 14/220,706, filed on Mar. 20, 2014, now Pat. No. 10,245,184, which is a
(Continued)

(51) Int. Cl.
*A61M 1/00* (2006.01)
*A61F 13/02* (2006.01)
(Continued)

(52) U.S. Cl.
CPC .. *A61F 13/00059* (2013.01); *A61F 13/00017* (2013.01); *A61F 13/00029* (2013.01);
(Continued)

(58) Field of Classification Search
CPC ......... A61M 1/00; A61M 27/00; A61F 13/02; A61F 13/00017; A61F 13/00029;
(Continued)

(56) References Cited

U.S. PATENT DOCUMENTS 1,195,430 A 8/1916 Angier
1,355,846 A 10/1920 Rannells
(Continued)

FOREIGN PATENT DOCUMENTS

AU 550575 B2 3/1986
AU 745271 B2 3/2002
(Continued)

OTHER PUBLICATIONS

A Prospective, Blinded, Randomized, Controlled Clinical Trial of Topical Negative Pressure Use in Skin Grafting, Elias Moisidis, Tim Heath, Catherine Boorer, Kevin Ho, Anand K. Deva, Sydney, Australia, From the Department of Plastic and Maxillofacial Surgery, Liverpool Hospital. Mar. 25, 2003; revised Oct. 1, 2003.
(Continued)

*Primary Examiner* — Tatyana Zalukaeva
*Assistant Examiner* — Ilya Y Treyger

(57) ABSTRACT

A system for providing reduced-pressure treatment to a moveable tissue site, such as a joint, includes a flexible dressing bolster. The flexible dressing bolster has a first side and a second, inward-facing side, and a plurality of flexion joints formed on the flexible dressing bolster. The system further includes a sealing subsystem for providing a fluid seal over the flexible dressing bolster and the patient's epidermis and a reduced-pressure subsystem for delivering a reduced pressure to the sealing subsystem. The sealing subsystem and reduced-pressure subsystem are operable to deliver a reduced pressure to the moveable tissue site. The flexible dressing bolster is operable to allow articulation or
(Continued)

movement of the moveable tissue site. The sealing subsystem may include a drape with folds. Other systems, apparatuses, and methods are presented.

24 Claims, 12 Drawing Sheets

Related U.S. Application Data continuation of application No. 13/363,889, filed on Feb. 1, 2012, now Pat. No. 8,715,253, which is a division of application No. 12/475,407, filed on May 29, 2009, now Pat. No. 8,133,211.

(60) Provisional application No. 61/144,067, filed on Jan. 12, 2009, provisional application No. 61/121,362, filed on Dec. 10, 2008, provisional application No. 61/057,797, filed on May 30, 2008, provisional application No. 61/057,798, filed on May 30, 2008, provisional application No. 61/057,800, filed on May 30, 2008, provisional application No. 61/057,802, filed on May 30, 2008, provisional application No. 61/057,803, filed on May 30, 2008, provisional application No. 61/057,805, filed on May 30, 2008, provisional application No. 61/057,807, filed on May 30, 2008, provisional application No. 61/057,808, filed on May 30, 2008, provisional application No. 61/057,810, filed on May 30, 2008.

(51) Int. Cl.
*A61F 13/00* (2006.01)
*A61L 15/60* (2006.01)
*A61H 1/00* (2006.01)
*A61F 15/00* (2006.01)
*A61M 27/00* (2006.01)
*A61L 15/16* (2006.01)

(52) U.S. Cl.
CPC .. *A61F 13/00034* (2013.01); *A61F 13/00038* (2013.01); *A61F 13/00068* (2013.01); *A61F 13/022* (2013.01); *A61F 13/0209* (2013.01); *A61F 13/0216* (2013.01); *A61F 13/0223* (2013.01); *A61F 13/0243* (2013.01); *A61F 13/0289* (2013.01); *A61F 15/008* (2013.01); *A61H 1/008* (2013.01); *A61L 15/60* (2013.01); *A61M 1/0023* (2013.01); *A61M 1/71* (2021.05); *A61M 1/90* (2021.05); *H05K 999/99* (2013.01); *A61F 13/00* (2013.01); A61F 2013/0028 (2013.01); A61F 2013/0054 (2013.01); A61F 2013/00131 (2013.01); A61F 2013/00136 (2013.01); A61F 2013/00174 (2013.01); A61F 2013/00182 (2013.01); A61F 2013/00246 (2013.01); A61F 2013/00536 (2013.01); A61F 2013/00748 (2013.01); A61M 2205/70 (2013.01); A61M 2207/00 (2013.01); A61M 2210/1007 (2013.01); A61M 2210/1021 (2013.01); *Y10T 29/49* (2015.01); *Y10T 29/49826* (2015.01)

(58) Field of Classification Search
CPC .......... A61F 13/00034; A61F 13/00038; A61F 13/00068; A61F 13/0209; A61F 13/0216; A61F 13/0223; A61L 15/16
See application file for complete search history.

(56) References Cited

U.S. PATENT DOCUMENTS

| | | |
|---|---|---|
| 1,638,043 A | 8/1927 | Lee |
| 1,845,630 A | 2/1932 | Scholl |
| 2,452,345 A | 10/1948 | Ceyl |
| 2,547,758 A | 4/1951 | Keeling |
| 2,632,443 A | 3/1953 | Lesher |
| 2,682,873 A | 7/1954 | Evans et al. |
| 2,896,618 A | 7/1959 | Schaefer |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |
| 3,367,332 A | 2/1968 | Groves |
| 3,419,006 A | 12/1968 | Warwick |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,892,229 A | 7/1975 | Taylor et al. |
| 3,903,882 A | 9/1975 | Augurt |
| 3,969,561 A | 7/1976 | Marshall |
| 4,080,970 A | 3/1978 | Miller |
| 4,091,804 A | 5/1978 | Hasty |
| 4,096,853 A | 6/1978 | Weigand |
| 4,121,582 A | 10/1978 | Masso Remiro |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,430,998 A | 2/1984 | Harvey et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,572,814 A | 2/1986 | Naylor et al. |
| 4,605,399 A | 8/1986 | Weston et al. |
| 4,608,041 A | 8/1986 | Nielsen |
| 4,612,230 A | 9/1986 | Liland et al. |
| 4,640,688 A | 2/1987 | Hauser |
| 4,655,754 A | 4/1987 | Richmond et al. |
| 4,663,352 A | 5/1987 | Onofrj |
| 4,664,662 A | 5/1987 | Webster |
| 4,710,165 A | 12/1987 | McNeil et al. |
| 4,722,332 A | 2/1988 | Saggers |
| 4,727,868 A | 3/1988 | Szycher et al. |
| 4,733,659 A | 3/1988 | Edenbaum et al. |
| 4,743,232 A | 5/1988 | Kruger |
| 4,751,133 A | 6/1988 | Szycher et al. |
| 4,758,220 A | 7/1988 | Sundblom et al. |
| 4,770,490 A | 9/1988 | Gruenewald et al. |
| 4,787,888 A | 11/1988 | Fox |
| 4,795,435 A | 1/1989 | Steer |
| 4,826,494 A | 5/1989 | Richmond et al. |
| 4,838,883 A | 6/1989 | Matsuura |

(56) References Cited

U.S. PATENT DOCUMENTS

| | | |
|---|---|---|
| 4,840,187 A | 6/1989 | Brazier |
| 4,863,449 A | 9/1989 | Therriault et al. |
| 4,865,026 A | 9/1989 | Barrett |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,741 A | 3/1991 | Kalt |
| 5,018,515 A | 5/1991 | Gilman |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,306,798 A | 4/1994 | Horn et al. |
| 5,342,376 A | 8/1994 | Ruff |
| 5,344,415 A | 9/1994 | DeBusk et al. |
| 5,358,494 A | 10/1994 | Svedman |
| 5,376,067 A | 12/1994 | Daneshvar |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,653,244 A | 8/1997 | Shaw |
| 5,714,225 A | 2/1998 | Hansen et al. |
| 5,792,088 A | 8/1998 | Felder et al. |
| 5,844,013 A | 12/1998 | Kenndoff et al. |
| 5,866,249 A | 2/1999 | Yarusso et al. |
| 5,944,017 A | 8/1999 | Tweedle |
| 5,950,238 A | 9/1999 | Klein |
| 5,973,221 A | 10/1999 | Collyer et al. |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,162,960 A | 12/2000 | Klein |
| 6,176,868 B1 | 1/2001 | Detour |
| 6,213,840 B1 | 4/2001 | Han |
| 6,241,747 B1 | 6/2001 | Ruff |
| 6,270,910 B1 | 8/2001 | Jaeger et al. |
| 6,287,316 B1 | 9/2001 | Agarwal et al. |
| 6,345,623 B1 | 2/2002 | Heaton et al. |
| 6,361,397 B1 | 3/2002 | Mankovitz et al. |
| 6,420,622 B1 | 7/2002 | Johnston et al. |
| 6,426,931 B1 | 7/2002 | Parienti |
| 6,440,093 B1 | 8/2002 | McEwen et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,500,112 B1 | 12/2002 | Khouri |
| 6,528,697 B1 | 3/2003 | Knutson et al. |
| 6,553,998 B2 | 4/2003 | Heaton et al. |
| 6,566,576 B1 | 5/2003 | Komerska et al. |
| 6,648,862 B2 | 11/2003 | Watson |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,867,342 B2 | 3/2005 | Johnston et al. |
| D503,509 S | 4/2005 | Bell et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,070,584 B2 | 7/2006 | Johnson et al. |
| 7,090,647 B2 | 8/2006 | Mimura et al. |
| 7,135,007 B2 | 11/2006 | Scott et al. |
| 7,144,294 B2 | 12/2006 | Bell et al. |
| 7,195,624 B2 | 3/2007 | Lockwood et al. |
| 7,201,063 B2 | 4/2007 | Taylor |
| 7,201,263 B2 | 4/2007 | Osada et al. |
| 7,214,202 B1 | 5/2007 | Vogel et al. |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,455,681 B2 | 11/2008 | Wilke et al. |
| 7,504,549 B2 | 3/2009 | Castellani et al. |
| 7,520,872 B2 | 4/2009 | Biggie et al. |
| 7,532,953 B2 | 5/2009 | Vogel |
| 7,534,927 B2 | 5/2009 | Lockwood et al. |
| 7,569,742 B2 | 8/2009 | Haggstrom et al. |
| 7,699,831 B2 | 4/2010 | Bengtson et al. |
| 7,700,819 B2 | 4/2010 | Ambrosio et al. |
| 7,846,141 B2 | 12/2010 | Weston |
| 8,062,273 B2 | 11/2011 | Weston |
| 8,100,848 B2 | 1/2012 | Wilkes et al. |
| 8,129,580 B2 | 3/2012 | Wilkes et al. |
| 8,216,198 B2 | 7/2012 | Heagle et al. |
| 8,241,261 B2 | 8/2012 | Randolph et al. |
| 8,251,979 B2 | 8/2012 | Malhi |
| 8,257,327 B2 | 9/2012 | Blott et al. |
| 8,398,614 B2 | 3/2013 | Blott et al. |
| 8,399,730 B2 | 3/2013 | Kazala, Jr. et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,641,691 B2 | 2/2014 | Fink et al. |
| 8,679,081 B2 | 3/2014 | Heagle et al. |
| 8,722,959 B2 | 5/2014 | Wilkes et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,044,579 B2 * | 6/2015 | Blott ................. A61F 13/00068 |
| 9,095,468 B2 | 8/2015 | Kazala, Jr. et al. |
| 9,198,801 B2 | 12/2015 | Weston |
| 9,211,365 B2 | 12/2015 | Weston |
| 9,289,542 B2 | 3/2016 | Blott et al. |
| 9,456,928 B2 * | 10/2016 | Haggstrom ........... A61M 39/24 |
| 9,572,719 B2 | 2/2017 | Long et al. |
| 9,750,641 B2 | 9/2017 | Kazala, Jr. et al. |
| 10,143,593 B2 | 12/2018 | Kazala, Jr. et al. |
| 2001/0029956 A1 | 10/2001 | Argenta et al. |
| 2001/0043943 A1 | 11/2001 | Coffey |
| 2002/0007014 A1 | 1/2002 | Hyde et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040691 A1 | 2/2003 | Griesbach et al. |

(56) References Cited

U.S. PATENT DOCUMENTS

| | | |
|---|---|---|
| 2003/0109816 A1 | 6/2003 | Lachenbruch et al. |
| 2003/0139697 A1 | 7/2003 | Gilman |
| 2003/0212359 A1 | 11/2003 | Butler |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0127836 A1 | 7/2004 | Sigurjonsson et al. |
| 2004/0242119 A1 | 12/2004 | Francis |
| 2004/0243073 A1 | 12/2004 | Lockwood et al. |
| 2005/0059918 A1 | 3/2005 | Sigurjonsson et al. |
| 2005/0070858 A1 | 3/2005 | Lockwood et al. |
| 2005/0101940 A1 | 5/2005 | Radl et al. |
| 2005/0142331 A1 | 6/2005 | Anderson et al. |
| 2005/0209574 A1 | 9/2005 | Boehringer et al. |
| 2005/0222544 A1 | 10/2005 | Weston |
| 2005/0228329 A1 | 10/2005 | Boehringer et al. |
| 2006/0041247 A1 | 2/2006 | Petrosenko et al. |
| 2006/0064049 A1 | 3/2006 | Marcussen |
| 2006/0079852 A1 | 4/2006 | Bubb et al. |
| 2006/0149171 A1 | 7/2006 | Vogel et al. |
| 2006/0173253 A1 | 8/2006 | Ganapathy et al. |
| 2006/0189910 A1 | 8/2006 | Johnson et al. |
| 2006/0213527 A1 | 9/2006 | Argenta et al. |
| 2006/0264796 A1 | 11/2006 | Flick et al. |
| 2007/0021697 A1 | 1/2007 | Ginther et al. |
| 2007/0027414 A1 | 2/2007 | Hoffman et al. |
| 2007/0032755 A1 | 2/2007 | Walsh |
| 2007/0044801 A1* | 3/2007 | Mathis ............... A41D 13/11 128/206.19 |
| 2007/0066946 A1 | 3/2007 | Haggstrom et al. |
| 2007/0078366 A1 | 4/2007 | Haggstrom et al. |
| 2007/0129707 A1 | 6/2007 | Blott et al. |
| 2007/0135777 A1 | 6/2007 | Greene et al. |
| 2007/0167884 A1 | 7/2007 | Mangrum et al. |
| 2007/0185426 A1 | 8/2007 | Ambrosio et al. |
| 2007/0185463 A1 | 8/2007 | Mulligan |
| 2007/0219497 A1 | 9/2007 | Johnson et al. |
| 2007/0219513 A1 | 9/2007 | Lina et al. |
| 2007/0219532 A1 | 9/2007 | Karpowicz et al. |
| 2007/0225663 A1 | 9/2007 | Watt et al. |
| 2007/0255193 A1 | 11/2007 | Patel et al. |
| 2008/0004549 A1 | 1/2008 | Anderson et al. |
| 2008/0009812 A1 | 1/2008 | Riesinger |
| 2008/0026023 A1 | 1/2008 | Tauer et al. |
| 2008/0039763 A1 | 2/2008 | Sigurjonsson et al. |
| 2008/0071207 A1 | 3/2008 | de Luis et al. |
| 2008/0071214 A1 | 3/2008 | Locke et al. |
| 2008/0076844 A1 | 3/2008 | Van Sumeren et al. |
| 2008/0103462 A1 | 5/2008 | Wenzel et al. |
| 2008/0103489 A1 | 5/2008 | Dahners |
| 2008/0119802 A1 | 5/2008 | Riesinger |
| 2009/0043268 A1 | 2/2009 | Eddy et al. |
| 2009/0047855 A1 | 2/2009 | Seth et al. |
| 2009/0125004 A1 | 5/2009 | Shen et al. |
| 2009/0177051 A1 | 7/2009 | Arons et al. |
| 2009/0204084 A1 | 8/2009 | Blott et al. |
| 2009/0204085 A1 | 8/2009 | Biggie et al. |
| 2009/0227968 A1 | 9/2009 | Vess |
| 2009/0234307 A1 | 9/2009 | Vitaris |
| 2009/0264807 A1 | 10/2009 | Haggstrom et al. |
| 2009/0293887 A1 | 12/2009 | Wilkes et al. |
| 2009/0299257 A1 | 12/2009 | Long et al. |
| 2012/0220963 A1 | 8/2012 | Hunt et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CA | 2468309 A1 | 7/2003 |
| CA | 2560068 A1 | 10/2005 |
| CA | 2651833 A1 | 11/2007 |
| CN | 1545991 A | 11/2004 |
| CN | 101277734 A | 10/2008 |
| DE | 26 40 413 A1 | 3/1978 |
| DE | 39 07 522 C1 | 4/1990 |
| DE | 43 06 478 A1 | 9/1994 |
| DE | 29 504 378 U1 | 9/1995 |
| DE | 20 2006 007877 U1 | 7/2006 |
| DE | 102005007016 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0421465 A2 | 4/1991 |
| EP | 0424165 A1 | 4/1991 |
| EP | 0619105 A1 | 10/1994 |
| EP | 0691113 A1 | 1/1996 |
| EP | 0756854 A1 | 2/1997 |
| EP | 1018967 A1 | 7/2000 |
| EP | 2282788 B1 | 12/2016 |
| FR | 1163907 A | 10/1958 |
| FR | 2661821 A1 | 11/1991 |
| GB | 692578 A | 6/1953 |
| GB | 1574066 A | 9/1980 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | H08154964 A | 6/1996 |
| JP | H10356 A | 1/1998 |
| JP | 2000-189427 A | 7/2000 |
| JP | 2000210386 A | 8/2000 |
| JP | 2002-078730 A | 3/2002 |
| JP | 2003-116907 A | 4/2003 |
| JP | 2004-160220 A | 6/2004 |
| JP | 2006-141908 A | 6/2006 |
| JP | 2006219776 A | 8/2006 |
| JP | 2006239213 A | 9/2006 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 92/05755 A1 | 4/1992 |
| WO | 1993/000056 A1 | 1/1993 |
| WO | 93/009727 A1 | 5/1993 |
| WO | 199415562 A1 | 7/1994 |
| WO | 94/020041 A1 | 9/1994 |
| WO | 199420152 A1 | 9/1994 |
| WO | 1995/14451 A1 | 6/1995 |
| WO | 96/05873 A1 | 2/1996 |
| WO | 1997005838 A1 | 2/1997 |
| WO | 1997/11658 A1 | 4/1997 |
| WO | 97/18007 A1 | 5/1997 |
| WO | 99/01173 A1 | 1/1999 |
| WO | 99/13793 A1 | 3/1999 |
| WO | 0007653 A1 | 2/2000 |
| WO | 2000061206 A1 | 10/2000 |
| WO | 2001/02478 A1 | 1/2001 |
| WO | 01/034223 A1 | 5/2001 |
| WO | 2001/89431 A1 | 11/2001 |
| WO | 200185248 A1 | 11/2001 |
| WO | 2002/20067 A2 | 3/2002 |
| WO | 2002/083046 A1 | 10/2002 |
| WO | 2003017898 A1 | 3/2003 |
| WO | 2003/057071 A2 | 7/2003 |
| WO | 2003/057307 A1 | 7/2003 |
| WO | 03070135 A2 | 8/2003 |
| WO | 2003077989 A1 | 9/2003 |
| WO | 2003/086262 A1 | 10/2003 |
| WO | 2003101385 A2 | 12/2003 |
| WO | 2004/047695 A1 | 6/2004 |
| WO | 2004/060413 A1 | 7/2004 |
| WO | 2005025447 A2 | 3/2005 |
| WO | 2005034797 A2 | 4/2005 |
| WO | 2005051461 A1 | 6/2005 |

(56) References Cited

FOREIGN PATENT DOCUMENTS

| WO | 2005082435 A1 | 9/2005 |
|---|---|---|
| WO | 2005/091884 A2 | 10/2005 |
| WO | 2005/123170 A1 | 12/2005 |
| WO | 2006/012745 A1 | 2/2006 |
| WO | 2007030599 A2 | 3/2007 |
| WO | 2007031762 A1 | 3/2007 |
| WO | 2007033679 A2 | 3/2007 |
| WO | 2007/041642 A2 | 4/2007 |
| WO | 2007085396 A1 | 8/2007 |
| WO | 2007/120138 A2 | 10/2007 |
| WO | 2008013869 A2 | 1/2008 |
| WO | 2008013896 A2 | 1/2008 |
| WO | 2008/020209 A2 | 2/2008 |
| WO | 2008041926 A1 | 4/2008 |
| WO | 2008054312 A1 | 5/2008 |
| WO | 2008063281 A2 | 5/2008 |
| WO | 2008/104609 A1 | 9/2008 |
| WO | 2009019496 A2 | 2/2009 |
| WO | 2009/047524 A2 | 4/2009 |
| WO | 2009/071926 A1 | 6/2009 |

OTHER PUBLICATIONS

The Vacuum Assisted Closure Device, A Method of Securing Skin Grafts and Improving Grafts Survival; Lynette A. Scherer, MD; Stephen Shiver, MD; Michael Chang, MD; J_ Wayne Meredith, MD; John T. Owings. MD; From the Departments of Surgery, University of California-Davis Medical Center, Sacramento (Ors. Sherer and Owings), and Wake Forest University Baptist Medical Center, Winston-Salem, NC (Ors. Shiver, Chang, and Meredith); Arch SurQNol 137, AuQ 2002; www.archsurQ.com.
Laskin, et al.; "Minimally Invasive Total Knee Replacement Through a Mini-Midvastus Incision: An Outcome Study," Surgical Technology International XIII, 2004; 231-8.
A. Dee, "The successful management of a dehisced surgical wound with TNP following Femoropopliteal bypass", Journal of Wound Care, vol. 16, No. 1, Jan. 2007.
Ogazon, Use of Vacuum-Assisted Closure in the Treatment of Surgical Infection Sites Cir. Mar.-Apr. 2006; 74(2): 107-13 (Spanish).
Timmenga, "The Effects of Mechanical Stress on Healing Skin Wounds: An Experimental Study in Rabbits Using Tissues Expansions," British Journal of Plastic Surgery 1991; 44(7): 514-519.
Cunningham "Development of in-vitro Model to Simulate Dermal Wound Bed Interaction with GranuFoam and Gauze Dressing under Sub Atmospheric Pressure" RPT 111-05-02, Device Implant Innovations 2006.
Delalleau, A., et al., "Characterization of the Mechanical Properties of Skin by Inverse Analysis Combined with the Indentation Test" Journal of Biomechanics, 2006; pp. 1603-1610.
Pailler-Mattei, C., "Caracte; Risation Me' Canique et Tribologizue de la Peau Humain In Vivo", 2004-31.
Khatyr, F., "Model of the Viscoelastic Behavior of Skin In Vivo and Study of Anisotropy", Skin Research and Technology 2004; pp. 96-103.
Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behavior of Biomedical Materials (2008), pp. 1-16.
Diridollou, "In vivo Model of the Mechanical Properties of the Human Skin under Suction", Skin Research and Technology, 2000; 6:214-221.
Woo, "Structural Model to Describe the Non-Linear Stress-Strain Behavior for Parallel-Fibered Collagenous Tissues," Journal of Biomechanical Engineering, Nov. 1989, vol. 111/361.
International Search Report and Written Opinion dated Oct. 20, 2009; PCT International Application No. PCT/US2009/045747.

International Search Report and Written Opinion dated Oct. 16, 2009; PCT International Application No. PCT/US2009/045752.
International Search Report and Written Opinion dated Oct. 14, 2009; PCT International Application No. PCT/US2009/045746.
International Search Report and Written Opinion dated Oct. 27, 2009; PCT International Application No. PCT/US2009/045744.
International Search Report and Written Opinion dated Oct. 26, 2009; PCT International Application No. PCT/US2009/045751.
International Search Report and Written Opinion dated Oct. 21, 2009; PCT International Application No. PCT/US2009/045749.
International Search Report and Written Opinion dated Nov. 11, 2009; PCT International Application No. PCT/US2009/045754.
International Search Report and Written Opinion dated Nov. 12, 2009; PCT International Application No. PCT/US2009/045753.
International Search Report and Written Opinion dated Feb. 25, 2010; PCT International Application No. PCT/US2009/045750.
International Search Report and Written Opinion dated Mar. 12, 2010; PCT International Application No. PCT/US2009/045755.
Product Information for OptSiteTM dressing. Accessed Aug. 14, 2011.
International Search Report and Written Opinion dated Aug. 30, 2011 for PCT International Application No. PCT/US2011/034300.
International Search Report and Written Opinion dated Aug. 20, 2009; PCT International Application No. PCT/US2009/045743.
European Search Report for EP 09770665.9, dated Feb. 25, 2015.
Canadian Examiner's Report for Corresponding Application No. 2980359, dated Jul. 31, 2018.
Examination Report for corresponding EP 09770659.2, dated Sep. 4, 2013.
Extended European Search Report corresponding to Application No. 171645070, dated Jul. 18, 2017.
Extended European Search Report for corresponding Eurpean Application No. 12171212.9 dated Nov. 14, 2012.
European Search Report for EP 14182278.3 dated Jan. 7, 2015.
European Examination Report for corresponding EP09770663.4, dated Aug. 9, 2013.
Chintamani V.S. et al.: "Half Versus Full Vacuum Suction Drainage After Modified Radical Mastectomy for Breast Cancer—a Prospective Randomized Clinical Trial [ISRCTN24484328]", BMC Cancer, 2005, vol. 5, article 11; abstract.
Japanese Office Action corresponding to Application No. 2016104769, dated Mar. 7, 2017.
European Search Report for corresponding Application No. 16171527.1 dated Dec. 9, 2016.
Communication pursuant to Rule 114(2) EPC for corresponding EP Application 09770664.2, dated Aug. 22, 2013.
Canadian Office Action dated May 25, 2016, corresponding to Canada Application No. 2,725,945.
Mexican Office Action corresponding to Application No. MX/a/2010/013134, dated Oct. 26, 2017.
Indian Examination Report for corresponding Application No. 9029/DELNP/2010, dated Nov. 23, 2017.
Extended European Search Report for corresponding Application No. 161998968, dated Mar. 1, 2017.
Japanese Notice of Rejection Corresponding to Application No. 2017-235283, dated Aug. 6, 2019.
Extended European Search Report for corresponding Application No. 201963739, dated Jan. 1, 2021.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Japanese Notice of Rejection for corresponding Application No. 2020-005250, dated Oct. 27, 2020.
Chinese First Office Action for corresponding Application No. 202011083392.4, dated Aug. 2, 2021.

\* cited by examiner

REDUCED PRESSURE, COMPRESSION SYSTEMS AND APPARATUSES FOR USE ON JOINTS

RELATED APPLICATIONS

This application is a continuation of U.S. patent application Ser. No. 14/220,706, entitled "Reduced Pressure, Compression Systems and Apparatuses for Use on Joints," filed on Mar. 20, 2014, which is a continuation of U.S. patent application Ser. No. 13/363,889, entitled "Reduced Pressure, Compression Systems and Apparatuses for Use on Joints," filed on Feb. 1, 2012, which is a divisional of U.S. patent application Ser. No. 12/475,407, entitled "Reduced Pressure, Compression Systems and Apparatuses for Use on Joints," filed on May 29, 2009, now U.S. Pat. No. 8,133,211 on Mar. 13, 2012, which claims the benefit under 35 USC § 119(e), of the filing of U.S. Provisional Patent Application Ser. No. 61/144,067, entitled "Reduced-Pressure, Compression System and Apparatus for use on a Joint," filed Jan. 12, 2009; U.S. Provisional Patent Application Ser. No. 61/121,362, entitled "Reduced-Pressure Wound treatment System Employing an Anisotropic Drape," filed Dec. 10, 2008; U.S. Provisional Patent Application Ser. No. 61/057,802, entitled "Reduced-Pressure Dressing Assembly For Use in Applying a Closing Force," filed May 30, 2008; U.S. Provisional Patent Application Ser. No. 61/057,803, entitled "Reduced-Pressure, Linear-Wound Treatment System," filed May 30, 2008; U.S. Provisional Patent Application Ser. No. 61/057,807, entitled "Reduced-pressure Surgical Wound Treatment System," filed May 30, 2008; U.S. Provisional Patent Application Ser. No. 61/057,808, entitled "See-Through, Reduced-Pressure Dressing," filed May 30, 2008; U.S. Provisional Patent Application Ser. No. 61/057,810, entitled "Reduced-Pressure, Compression System and Apparatus for use on a Joint," filed May 30, 2008; U.S. Provisional Patent Application Ser. No. 61/057,800, entitled "Reduced-Pressure, Compression System and Apparatus for use on a Curved Body Part," filed, May 30, 2008; U.S. Provisional Patent Application serial number 61/057,798, entitled "Dressing Assembly For Subcutaneous Wound treatment Using Reduce Pressure," filed May 30, 2008; U.S. Provisional Patent Application Ser. No. 61/057,797, entitled "Reduced-Pressure, Compression System and Apparatus for use on Breast Tissue," filed May 30, 2008; and U.S. Provisional Patent Application Ser. No. 61/057,805, entitled "Super-Absorbent, Reduced-Pressure Wound Dressing and System," filed May 30, 2008. All of these applications are incorporated herein by reference for all purposes.

BACKGROUND

The present invention relates generally to medical systems, and more particularly, to reduced pressure, compression systems and apparatuses for use on joints.

Physicians perform millions of surgical procedures each year around the world. Many of the procedures are performed as open surgery and an increasing number are performed using minimally invasive surgery, such as arthroscopic, laparoscopic, and endoscopic procedures. Many of the surgical procedures involve surgery on a joint, such as arthroscopic knee surgery, arthroplasty, or many others.

Acute wounds are created during surgery, and these wounds require care for proper healing. In many situations, a sterile, dry gauze is merely applied. In some situations, a dressing is applied and a compression garment is applied. In the case of surgery on joints, the care of the resultant wounds can be more challenging because a dressing is desired that will allow movement of the joint. Consider as one example the context of knee surgery. The skin over the knee that is measured longitudinally while standing at seven inches stretches to nearly 15 inches when the knee is placed in a completely bent position. If that range of motion is desired, the dressing would need to be able to accommodate approximately a 100% stretch.

BRIEF SUMMARY

Shortcomings with devices, systems, and methods for wound care on a moveable tissue site, e.g., a joint, are addressed by the illustrative embodiments herein. According to an illustrative embodiment, a system for providing reduced-pressure treatment to a moveable tissue site includes a flexible dressing bolster having a first side and a second, inward-facing side and a plurality of flexion joints formed on the dressing bolster. The system further includes a sealing subsystem for providing a fluid seal over the flexible dressing bolster and a reduced-pressure subsystem for delivering a reduced pressure to the sealing subsystem. The sealing subsystem and reduced-pressure subsystem are operable to deliver a reduced pressure to the moveable tissue site. The flexible dressing bolster is operable to allow movement of the moveable tissue site.

According to one illustrative embodiment, flexible, reduced-pressure dressing assembly for use on a patient's joint includes a flexible bolster body having a first side and a second side. The bolster body is formed from a bolster material and has a first plurality of bolster modules formed on a first side of the bolster body, each bolster module having a bolster ridge. The dressing assembly further includes a drape extending over the bolster ridges of the first side of the bolster body. The drape is formed from an elastomeric material and is operable to stretch longitudinally at least 80 percent of the drape's un-stretched length.

According to one illustrative embodiment, flexible closing dressing bolster for use with a system for treating a linear wound on a patient's joint includes a bolster body having a first side and a second, inward-facing side, and is formed with a plurality of flexion joints. A first closing member is formed on the bolster body on a first longitudinal side of a center wound area. A second closing member is formed on the bolster body on a second longitudinal side of the center wound area. The first closing member and second closing member are operable to develop an inward closing force when the closing dressing bolster is placed under reduced pressure.

According to one illustrative embodiment, system for providing reduced-pressure wound treatment to a tissue site includes a flexible dressing bolster and a drape that at least partially covers the flexible dressing bolster. The drape includes a plurality of folds to facilitate bending of the tissue site. The system further includes a reduced-pressure source operable to deliver reduced pressure to the tissue site via the flexible dressing bolster.

According to one illustrative embodiment, an apparatus for providing reduced-pressure wound treatment to a tissue site includes a flexible dressing bolster having a first surface and a second, inward-facing surface. The flexible dressing bolster includes a plurality of flexion joints. The apparatus further includes a drape at least partially covers the bolster. The drape includes a plurality of drape-extension devices to facilitate bending of the apparatus.

Other features and advantages of the illustrative embodiments will become apparent with reference to the drawings and the detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
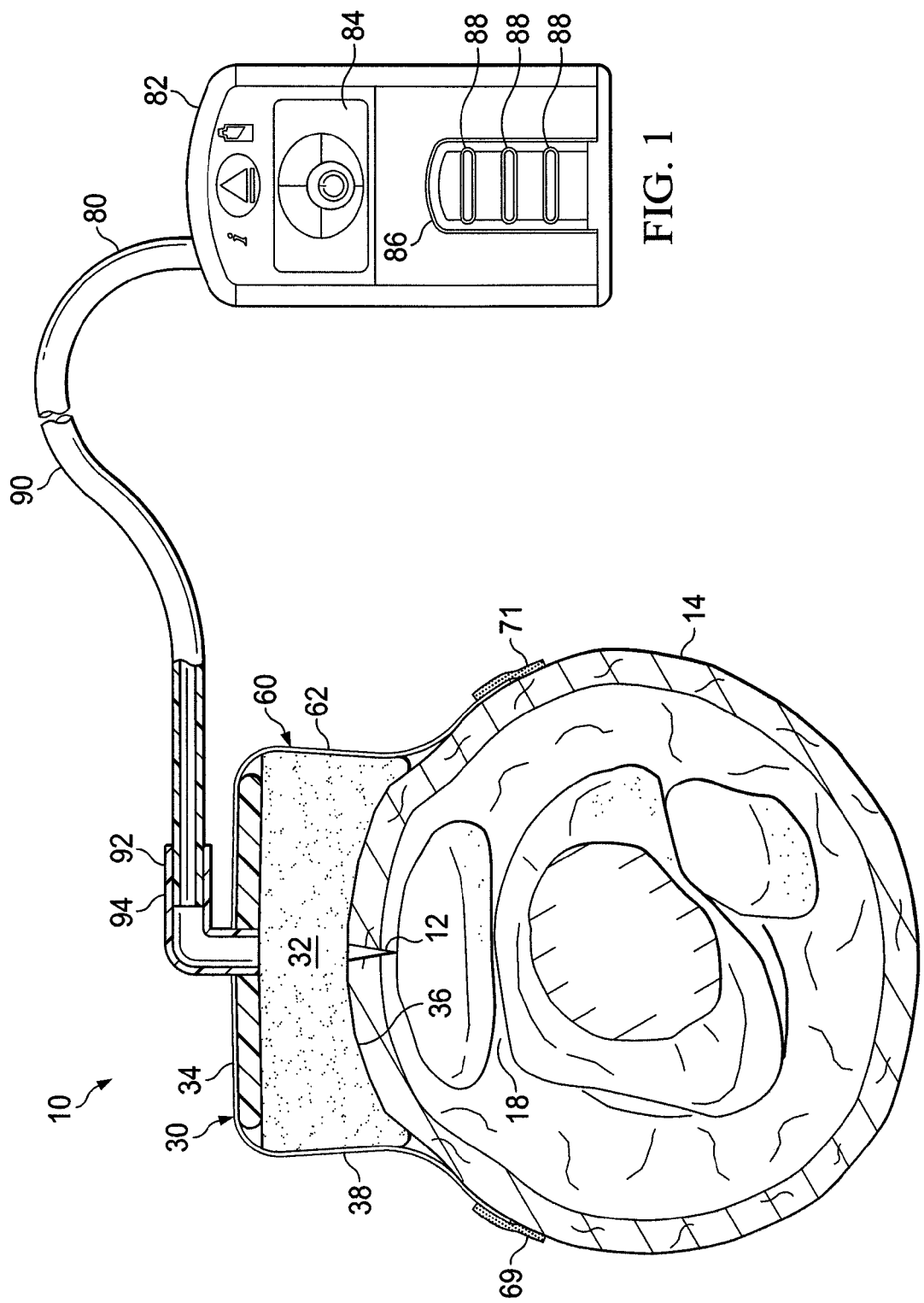
FIG. 1 is a schematic, lateral cross-section of one illustrative embodiment of a system for providing reduced-pressure wound therapy on a moveable tissue site.
Figure 2:
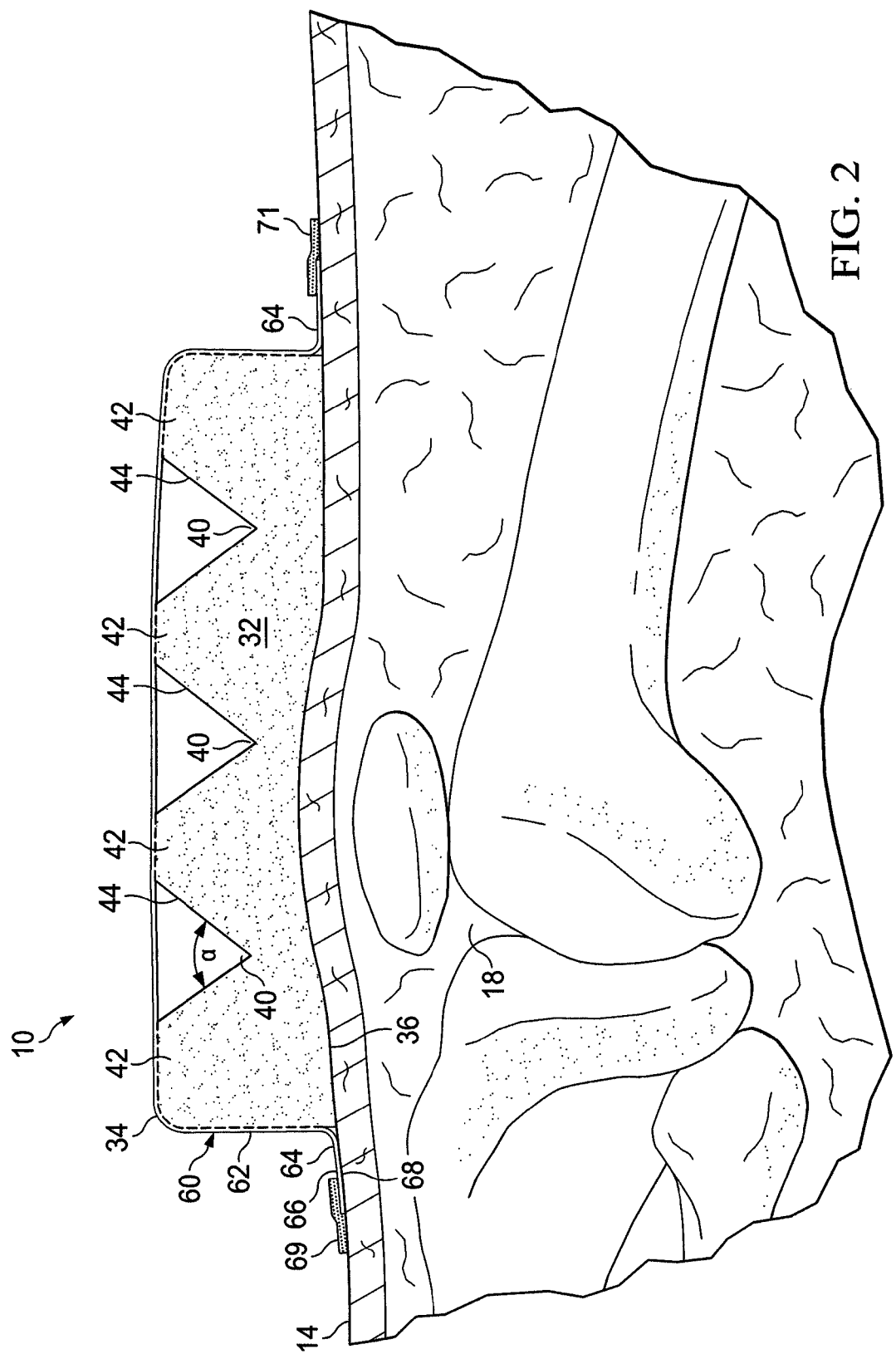
FIG. 2 is a schematic, longitudinal cross-section of a portion of the system of FIG. 1 on a knee in an extended (straight) position.
Figure 3:
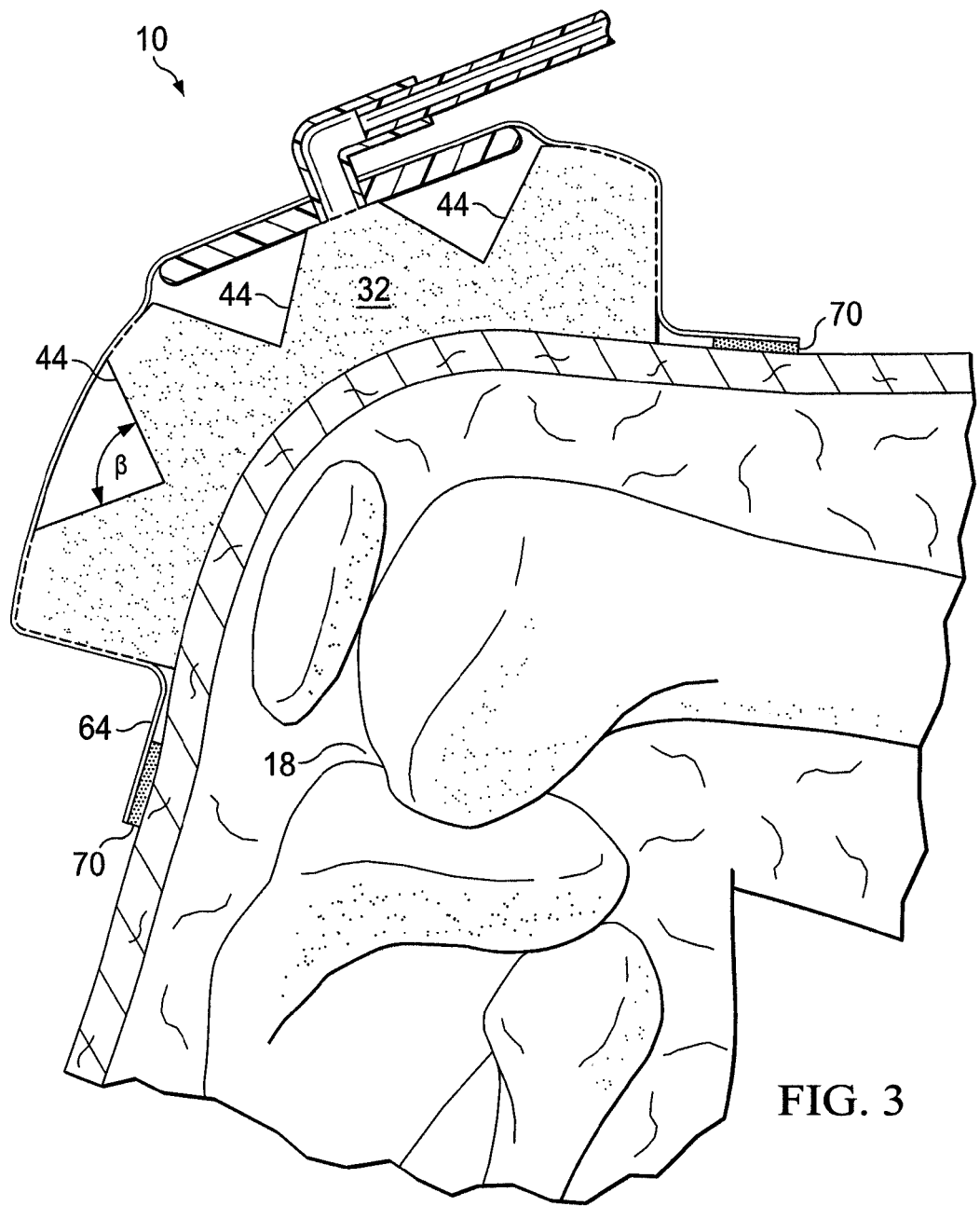
FIG. 3 is a schematic, longitudinal cross-section of the system of FIGS. 1 and 2 shown with the knee in the bent position.

Referring to FIGS. 1-3, a system 10 for applying a reduced pressure to a moveable tissue site, e.g., an incision 12 in a patient's epidermis 14 on or over a joint 18, is presented. The system 10 includes a flexible dressing assembly 30 that includes a flexible dressing bolster 32, a sealing subsystem 60, which includes a drape 62, and a reduced-pressure subsystem 80, which includes a reduced-pressure source 82 and reduced-pressure delivery conduit, or tubing 90.

The dressing assembly 30 includes a flexible dressing bolster 32 that has a first side 34 and a second, inward-facing, side 36. The flexible dressing bolster 32 has a peripheral edge 38. The flexible dressing bolster 32 may be made of a number of different bolster materials. In one embodiment, the flexible dressing bolster 32 may be made from a porous and permeable foam-like material and more particularly a reticulated, open-cell polyurethane or polyether foam that allows good permeability of wound fluids while under a reduced pressure. One such foam material is the VAC® Granufoam® Dressings available from KCI of San Antonio, Tex. Any material or combination of materials may be used for the bolster material provided that the bolster material is operable to manifold, or distribute, the reduced pressure. The bolster material may also be a combination or layering of materials. For example, a first bolster layer of hydrophilic foam may be disposed adjacent to a second bolster layer of hydrophobic foam to form the bolster material. The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include, without limitation, devices that have structural elements arranged to form flow channels, cellular foam such as open-cell foam, porous tissue collections, and liquids, gels and foams that include or cure to include flow channels.

The reticulated pores of the Granufoam® material, that are in the range of about 400 to 600 micron, are helpful in carrying out the manifold function, but other materials may be used. A material with a higher density (smaller pore size) than Granufoam® material may be preferable. The bolster material may be a reticulated foam that is later felted to a thickness of about ⅓ its original thickness. Among the many possible materials, the following may be used: Granufoam® material or a Foamex technical foam (www.foamex.com). In some instances it may be desirable to add ionic silver to the foam in a microbonding process or to add other substances to the bolster material such as antimicrobial agents. The bolster material may be isotropic or anisotropic depending on the exact orientation of the directed force, e.g., the compressive force, that is desired during reduced pressure. The bolster material could be a bio-absorbent material.

Formed on a first side 34 of flexible dressing bolster 32 is a plurality of flexion joints 40, or flexion areas. The flexion joints 40 are operable to allow the flexible dressing bolster 32 to flex as the underlying joint is rotated through its range of motion. The flexion joints 40 include a resting, or extended, angle of alpha (α) and when placed in motion has a bent angle beta (β) (FIG. 3). The flexion joints 40 may be formed in a number of different ways. One way to form the flexion joints 40 is to form a plurality of spaced bolster modules 42 that define a first plurality 44 of recesses, or notches, between bolster modules 42, and that have bolster ridges at an outer most portion, i.e., the top (for the orientation shown) of each bolster module 42. Additional recesses may be formed (e.g., see FIG. 5) and they may take on different shapes (e.g., see FIG. 7).

The sealing subsystem 60 includes a drape 62, or drape or sealing member. The drape 62 may be an elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, acrylic drape such as one available from Avery, or an incise drape.

The drape 62 may be disposed adjacent to or coupled to the flexible dressing bolster 32. As used herein, the term "coupled" includes coupling via a separate object, and also includes direct coupling. In the case of direct coupling, the two coupled objects touch each other in some way. The term "coupled" also encompasses two or more components that are continuous with one another by virtue of each of the components being formed from the same piece of material. Also, the term "coupled" includes chemical coupling, such as via a chemical bond. The term "coupled" may also include mechanical, thermal, or electrical coupling. "Coupled" may also mean fixedly coupled or removably coupled.

The coupling between the drape 62 and the flexible dressing bolster 32 may occur in many ways. For example, the drape 62 and the flexible dressing bolster 32 may be coupled using adhesives, such as by acrylic adhesive, silicone adhesive, hydrogel, hydrocolloid, etc. The drape 62 and the flexible dressing bolster 32 may be bonded by heat bonding, ultrasonic bonding, and radio frequency bonding, etc. The coupling may occur in patterns or completely. Structure may be added to the bond to make the drape 962 behave anisotropically in a desired direction, i.e., to make an isotropic drape material. An isotropic drape material helps the dressing assembly 30 to primarily move in a given direction, i.e., only about a certain axis or axes.

The drape 62 is sized to extend beyond a peripheral edge 38 of the flexible dressing bolster 32 and to thereby form a drape extension 64. The drape extension 64 has a first side 66 and a second, inward-facing side 68. The drape 62 may be sealed against the epidermis 14 of the patient using a sealing apparatus 69 for providing a fluid seal, which allows a reduced pressure to be maintained by the reduced-pressure subsystem 80. "Fluid seal," or "seal," means a seal adequate to maintain reduced pressure at a desired site given the particular reduced-pressure subsystem involved. The sealing apparatus 69 may take numerous forms, such as adhesive 70, a sealing tape, or drape tape, double-sided drape tape, paste, hydrocolloid, or other sealing means. If a tape is used, the tape may be formed from the same material as the drape 62 with a pre-applied, pressure-sensitive adhesive. The pressure sensitive adhesive 70 may be applied on the second side 68 of the drape extension 64. The pressure-sensitive adhesive 70 provides a substantially fluid-tight seal between the drape 62 and the epidermis 14 of the patient. Before the drape 62 is secured to the patient, the adhesive 70 may have removable strips covering the adhesive 70. For illustration purposes, FIGS. 1 and 2 are shown using a drape tape 71 and FIG. 3 is shown with an adhesive 70.

The reduced-pressure subsystem 80 includes a reduced-pressure source 82, or therapy unit, which can take many different embodiments that provide reduced pressure as a part of system 10. The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure source 82 provides reduced pressure for use within the system 10. The reduced-pressure source 82 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg. In order to maximize patient mobility and ease, the reduced-pressure source 82 is preferably a battery-powered, single-use reduced-pressure generator. Such a reduced-pressure source 82 facilitates application in the operating room and provides mobility and convenience for the patient during the rehabilitation phase. Other sources of reduced pressure may be utilized, such as the V.A.C.® therapy unit, which is available from KCI of San Antonio, Tex., or a wall suction unit. The reduced-pressure source 82 could also be supplied by a manually-operated, portable mechanical means, such as a piston in a tube, depending on how much leakage there is with the fluid seal.

The reduced-pressure source 82 is shown having a battery compartment 84 and a canister region 86 with windows 88 providing a visual indication of the level of fluid within canister region 86. An interposed membrane filter, such as hydrophobic or oleophobic filter, may be interspersed between a reduced-pressure delivery conduit, or tubing, 90 and the reduced-pressure source 82.

The reduced pressure developed by the reduced-pressure source 82 is delivered through the reduced-pressure delivery conduit 90 to a reduced-pressure interface 92, which may be an elbow port 94. In one embodiment, elbow port 94 is a TRAC® technology port available from KCI of San Antonio, Tex. The reduced-pressure interface 92 allows the reduced pressure to be delivered to the sealing subsystem 60 and realized within an interior portion of the sealing subsystem 60. In this particular embodiment, the elbow port 94 extends through or communicates through the drape 62 and into the flexible dressing bolster 32.

If the drape 62 is not already coupled, the drape 62 is placed over the first side 34 of the flexible dressing bolster 32 with an extra portion extending beyond the peripheral edge 38 to form the drape extension 64. The drape extension 64 may then be taped down (see 71 in FIG. 1) or an adhesive 70 (FIG. 3) used to form a fluid seal between the drape 62 and the patient's epidermis 14. The fluid seal need only be adequate to allow the system 10 to maintain a reduced pressure on the desired treatment area for a desired time frame. Indeed, some leakage allows for a low velocity air flow that may help with the healing process. The reduced-pressure interface 92 is applied if not already installed, and the reduced-pressure delivery conduit 90 is coupled at one end. The other end of the reduced-pressure delivery conduit 90 is coupled to the reduced-pressure source 82. The reduced-pressure source 82 may then be activated and reduced pressure delivered to the flexible dressing bolster 32. The reduced pressure may cause a directed force, which may include a compressive force or a closing force, to be developed on the tissue site, e.g., the wound. The force may be a compressive force or in some instance may be a lifting force as discussed further below. The embodiment shown presents a compressive force.

It may be desirable to apply the system 10 in the operating room and allow the system 10 to remain on the patient until adequate healing has taken place. In this regard, it may be desirable to form the drape 62, the flexible dressing bolster 32, and any other layers from transparent or translucent materials to allow the healthcare provider to gain visual cues about the healing of wounds without having to remove the dressing assembly 30.

As previously noted, the flexible dressing bolster 32 is adapted to allow the flexible dressing bolster 32 to flex, or move and stretch, with a moveable tissue site, e.g., one associated with an underlying joint 18, while providing reduced pressure to the incision 12. The resultant compression on the incision 12 and any undermined areas below the epidermis 14 as well as the reduced pressure supplied to the incision 12 help to remove any voids or defects and help to approximate the underlying tissues and the combined effect is to reduce edema and facilitate healing. A closing force may help strengthen the incision 12.

There are a number of ways to form the flexion joints and to otherwise help facilitate the flexing of the flexible dressing bolster 32. The formation of recesses 44, or notches, with the related bolster modules 42 on the first side 34 helps the flexible bolster 32 to bend with the joint 18. The angle between the bolster modules 42, that is the angle in the recess 44, is initially alpha ($\alpha$), and as the flexible bolster 32 is bent, the angle goes to a new angle beta ($\beta$) where beta ($\beta$) is greater than alpha ($\beta > \alpha$). In one illustrative embodiment, angle alpha ($\alpha$) is about 60 degrees and angle beta ($\beta$) is about ninety degrees. In another illustrative embodiment, angle alpha ($\alpha$) is about 30 degrees and angle beta ($\beta$) is about sixty degrees. Any of a wide range of possible angles are possible for angle alpha ($\alpha$) and angle beta ($\beta$).

The drape 62 may be coupled to the bolster modules 42. When a person's joint 18 is in the straight, or extended position, the drape 62 may go straight from one bolster module 42 to the next as shown in FIG. 2. In an alternative embodiment, the drape 62 may be coupled down in the recesses 44. In another embodiment, the drape 62 may form bubble ridges over the recesses 44.

Figure 4:
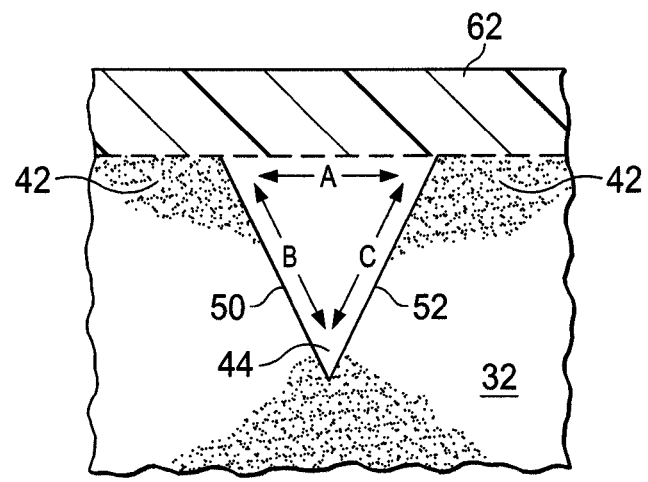
FIG. 4 is a schematic, cross-section of a portion of an illustrative embodiment of a flexible dressing assembly showing a recess.
Figure 8:
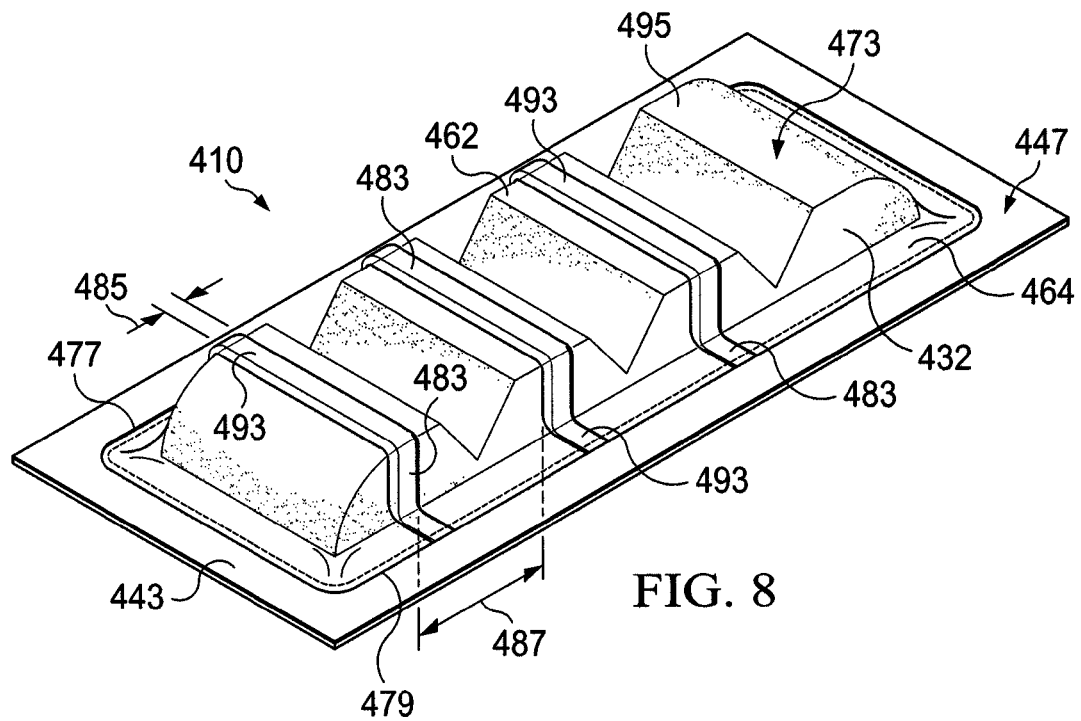
FIG. 8 is a schematic, perspective view of an apparatus for applying reduced pressure to a moveable tissue site according to an illustrative embodiment.
Figure 9:
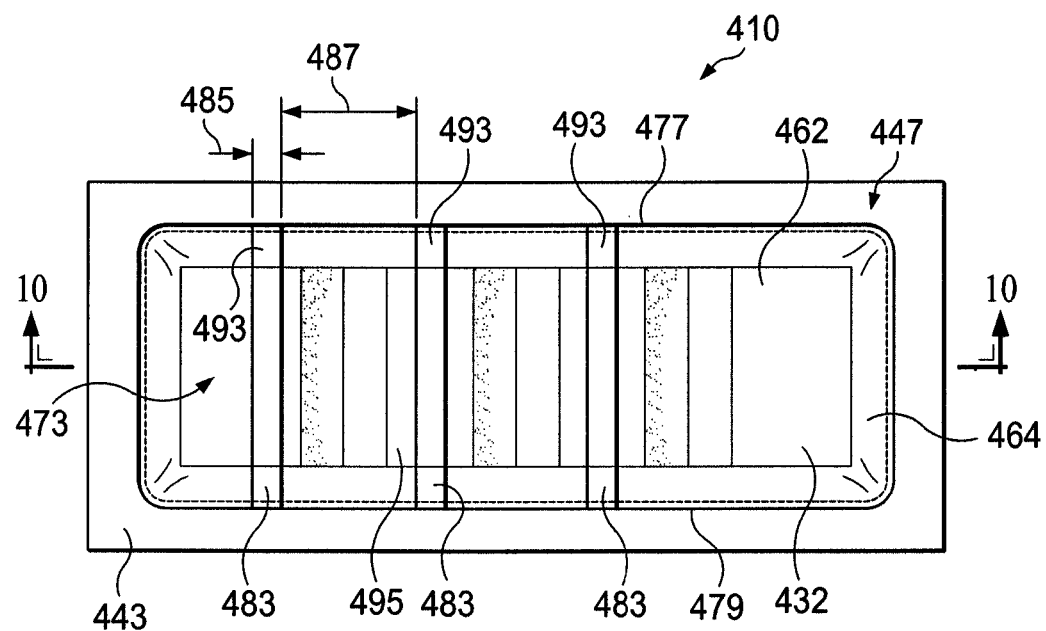
FIG. 9 is a schematic, plan view of the apparatus for applying reduced pressure to the tissue site of FIG. 8.

Referring now primarily to FIG. 4, a cross-section of a recess 44 is shown with a first side 50 and a second side 52. The first side 50 is shown having a dimension B and the second side 52 is shown with the dimension C. The third dimension A extends from the first side 50 to the second side 52 at the top to complete what is shown in cross-section as a triangle. The third side is covered by the drape 62. It will be appreciated that as the flexible dressing bolster 32 is flexed, sides 50 and 52 remain the same dimension substantially B, C, but the third dimension A grows. Thus, the drape 62 that is initially attached with a given dimension, must be able to stretch considerably. The drape 62 may need to stretch any where between 10% and 110% or more (e.g., 20%, 40%, 60%, 80%, 100%, 110% or even mores still) of the free (non-stretched) length of the drape 62. Indeed, dimension A can increase by more than one hundred percent during movement of some joints, and depending the particular embodiment, the drape 62 will need to accommodate the additional length. Alternatively or in addition, additional drape 62 material may be provided as described in connection with FIG. 8 below to facilitate extended dimension A.

Figure 5:
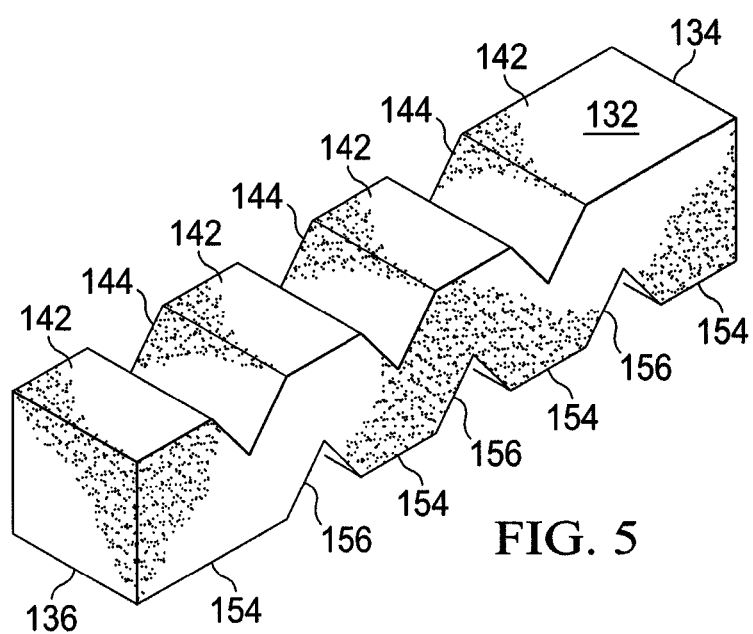
FIG. 5 is a schematic, perspective view of an illustrative embodiment of a flexible dressing bolster.

Referring now primarily to FIG. 5, another illustrative embodiment of a flexible bolster 132 is presented. The flexible dressing bolster 132 is analogous in most respects to the flexible dressing bolster 32 of the embodiment of FIGS. 1 through 3, but in addition to having a first plurality of bolster modules 142 with the related recesses 144 all formed on a first side 134 of the flexible dressing bolster 132, a second plurality of bolster modules 154 are formed on a second side 136 of the flexible dressing bolster 132. The bolster modules 154 have their concomitant bolster recesses 156.

Figure 6:
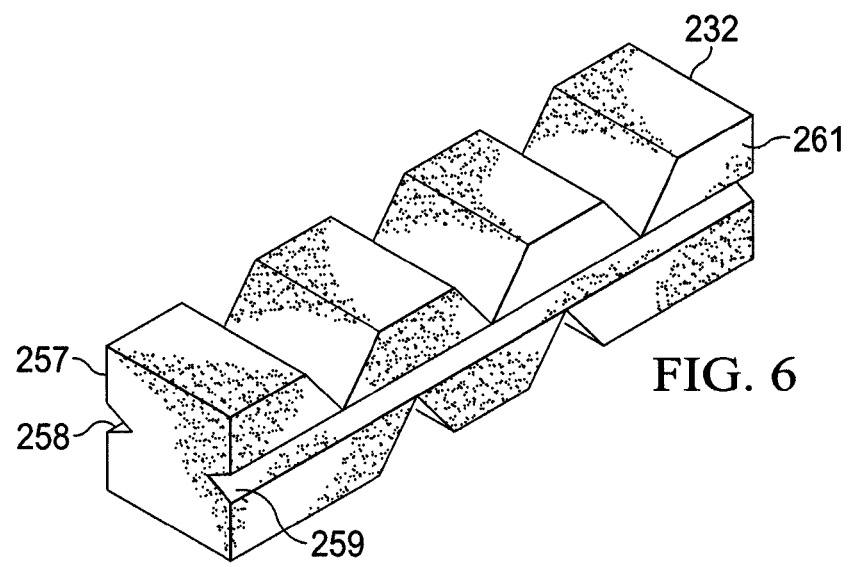
FIG. 6 is a schematic, perspective view of an illustrative embodiment of a flexible dressing bolster.

Referring primarily to FIG. 6, still another illustrative embodiment of a flexible bolster 232 is presented. The flexible dressing bolster 232 is identical to flexible dressing bolster 132 of FIG. 5 except that a first side recess 258 is formed on a first lateral side 257. In addition, a second side recess 259 is formed on a second lateral side 261.

Figure 7:
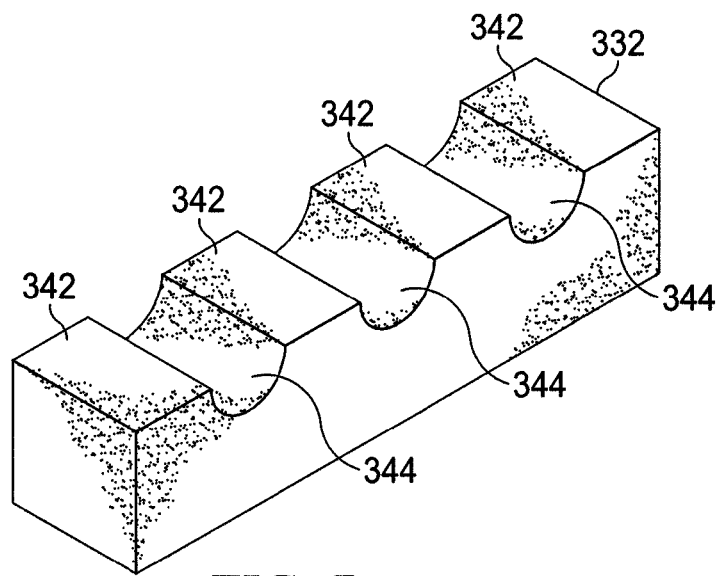
FIG. 7 is a schematic, perspective view of an illustrative embodiment of a flexible dressing bolster.

Referring now primarily to FIG. 7, another illustrative embodiment of a flexible dressing bolster 332 is presented. The flexible dressing bolster 332 includes bolster modules 342 and accompanying recesses 344, which in this embodiment are formed as semi-circular recesses. It should be noted that virtually any shape may be used for the recesses.

Figure 10A:
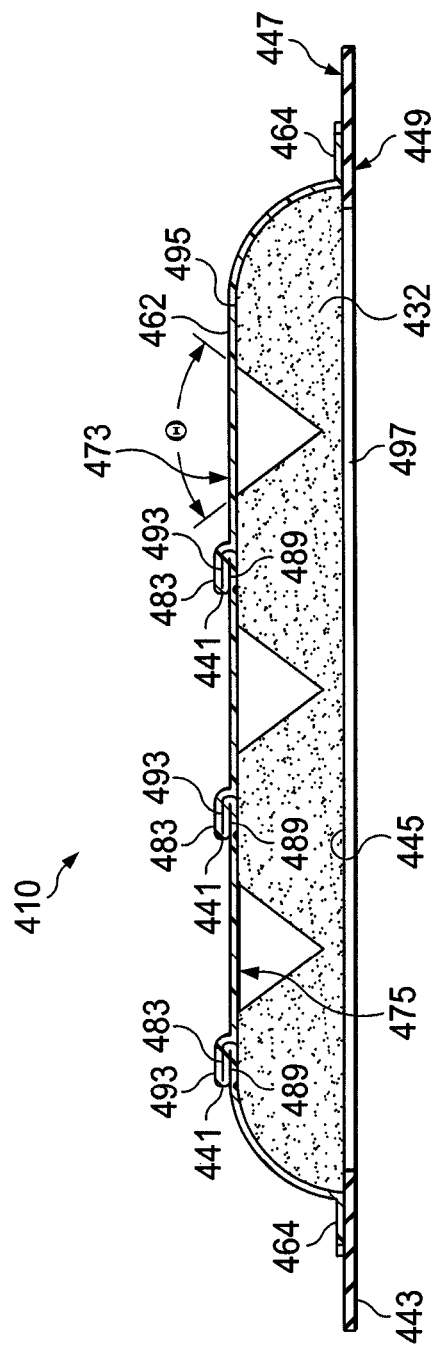
FIG. 10A is a schematic, longitudinal cross-sectional view of the apparatus in FIG. 9 taken along line 10-10 while the tissue site is in an extended (straight) position.
Figure 10B:
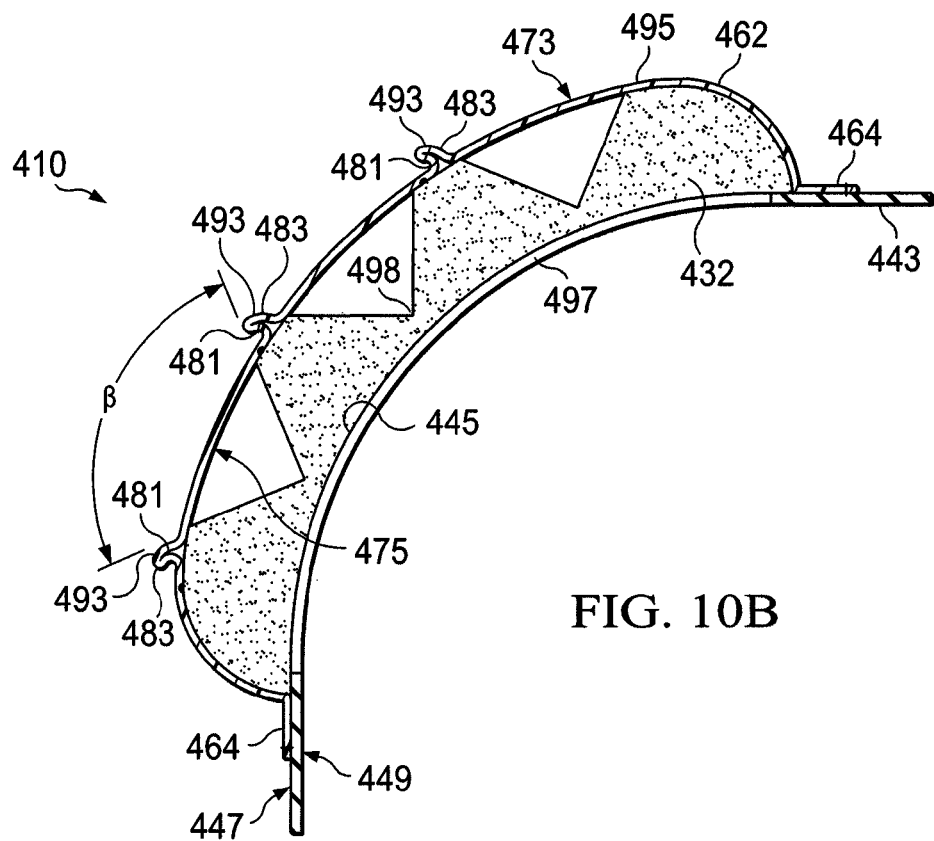
FIG. 10B is a schematic, longitudinal cross-sectional view of the apparatus in FIG. 9 taken along line 10-10 while the tissue site is in a bent position.

Referring now primarily to FIGS. 8-10B, an apparatus 410, or portion of a system, for applying reduced pressure to a moveable tissue site is shown according to an illustrative embodiment. The apparatus 410 includes a drape 462 that is disposed adjacent to or coupled to an intermediate drape layer 443 to form a pleated structure of drape 462 and to at least partially enclose a flexible dressing bolster 432. The pleated structure of drape 462 includes folds 493 that facilitate bending of the tissue site. As shown in FIG. 10B, the folds 493 may at least partially unfold when the tissue site is bent and increased tension is realized on a portion of the drape 462. The tissue site may be a joint, in which case the folds 493 readily facilitate articulation of the joint. However, the tissue site may also include any tissue capable of moving, stretching, or bending. The drape 462 and the flexible dressing bolster 432 are otherwise functionally analogous to the drapes and the bolsters previously shown in FIGS. 1-7 above.

The drape 462 may at least partially cover the flexible dressing bolster 432. The flexible dressing bolster 432 has a first side 495 and a second, inward-facing side 497. A plurality of flexion joints 498 are formed on the first side 495 of the flexible dressing bolster 432. The flexion joints 498 may be similar in function and design to the flexion joints 40 described previously herein.

In one embodiment, the drape 462 may partially or fully cover the first side 495 of the flexible dressing bolster 432.

In addition, the drape 462 may have a first side 473 and a second, bolster-facing side 475. The second side 475 of the drape 462 may be in direct or indirect contact with the flexible dressing bolster 432. Although the drape 462 may have a substantially rectangular shape as shown from the plan view of FIG. 9, the drape 462 may have any shape, such as a square, circular, elliptical, or polygonal shape.

The drape 462 includes lateral folds 493, each of which may extend from a first edge 477 of the drape 462 to a second, opposing edge 479 of the drape 462. The folds 493 may be formed by looping one or more portions 483 of the drape 462. Each of the folds 493 may also form a respective recess 481 in the drape 462 when the drape 462 is in the straight position or bent position.

Although the drape 462 is shown to include three folds 493, the drape 462 may include any number of folds. For example, the number of folds 493 may be varied to accommodate the range of motion of a tissue site, such as a particular joint.

The folds 493 may have any longitudinal length 485. For example, the longitudinal length 485 of each of the folds 493 may be substantially equal. In another example, each of the folds 493 may have a different longitudinal length 485. The longitudinal length 485 may also vary relative to the distance 487 between the folds 493. In one embodiment, the distance 487 between the folds 493 may be greater than the longitudinal length 485 of the folds 493. In another embodiment, the distance 487 between the folds 493 may be substantially equal to the longitudinal length 485 of the folds 493. In yet another embodiment, the longitudinal length 485 of the folds 493 may be larger than the distance 487 between the folds 493.

In one embodiment, the drape 462 may include bond sites 489 that are proximate the folds 493. The bond sites 489 may be operable to adhere each end 441 of the folds 493 to the first side 473 of the drape 462. The bond sites 489 may include any material capable of providing a bond between each end 441 of the folds 493 and the first side 473. During bending of the tissue site, as shown in FIG. 10B, each end 441 of the folds 493 may detach from the first side 473 of the drape 462.

Instead of being positioned externally on the first side 473 of the drape 462, the folds 493, in another embodiment, may be positioned within the flexion joints 498 of the flexible dressing bolster 432. Alternatively, the drape 462 may be substantially contoured to the first side 495 of the flexible dressing bolster 432 such that the drape 462 extends into the flexion joints 498 and is coupled to the flexible dressing bolster 432 within the flexion joints 498.

The apparatus 410 may also include an intermediate drape layer 443, which may include an aperture 445, or treatment-area aperture. The aperture 445 may provide fluid communication between the apparatus 410 and the tissue site. In one embodiment, the drape 462 may include a drape extension 464 around the perimeter of the drape 462. The drape extension 464 is similar to the drape extension 64 in FIGS. 2 and 3. The drape extension 464 may be coupled to the intermediate drape layer 443 such that the flexible dressing bolster 432 is at least partially enclosed by the drape 462 and the intermediate drape layer 443. The drape extension 464 may be coupled to the intermediate drape layer 443 as described in any of the illustrative embodiments, and may be coupled using RF welding, ultrasonic welding, an adhesive material, or any coupling mechanism.

The intermediate drape layer 443 includes a first side 447 and a second, inward-facing (tissue-facing) side 449. The second, inward-facing side 449 may include an adhesive. The second side, inward-facing 449 may adhere to the tissue site in a variety of ways, such as through the use of an adhesive material on the second side 449.

In one embodiment, the apparatus 410 may also include a tissue-interface layer (not shown) that is disposed between the flexible dressing bolster 432 and the tissue site. In one example of this embodiment, the tissue-interface layer may be disposed between the intermediate drape layer 443 and the tissue site. In another example, the tissue-interface layer may be at least partially disposed in the aperture 445.

In operation, the apparatus 410 may be applied to a tissue site that is moveable or bendable, such as a joint. The folds 493 of the drape 462 may unfold to accommodate bending of the tissue site, and thus allow the drape 462 to longitudinally elongate when the tissue site is bent. In one non-limiting example, as the tissue site is bent, the intermediate drape layer 443 may be elongated by an increase in arc length, thus causing the folds 493 of the drape 462, which is coupled to the intermediate drape layer 443 via the drape extension 464, to unfold. In this manner, the drape 462 may help to reduce the loading that is exerted onto the tissue site and surrounding area. Reduced pressure may also be applied to the tissue site as described in any illustrative embodiments disclosed herein.

Figure 11:
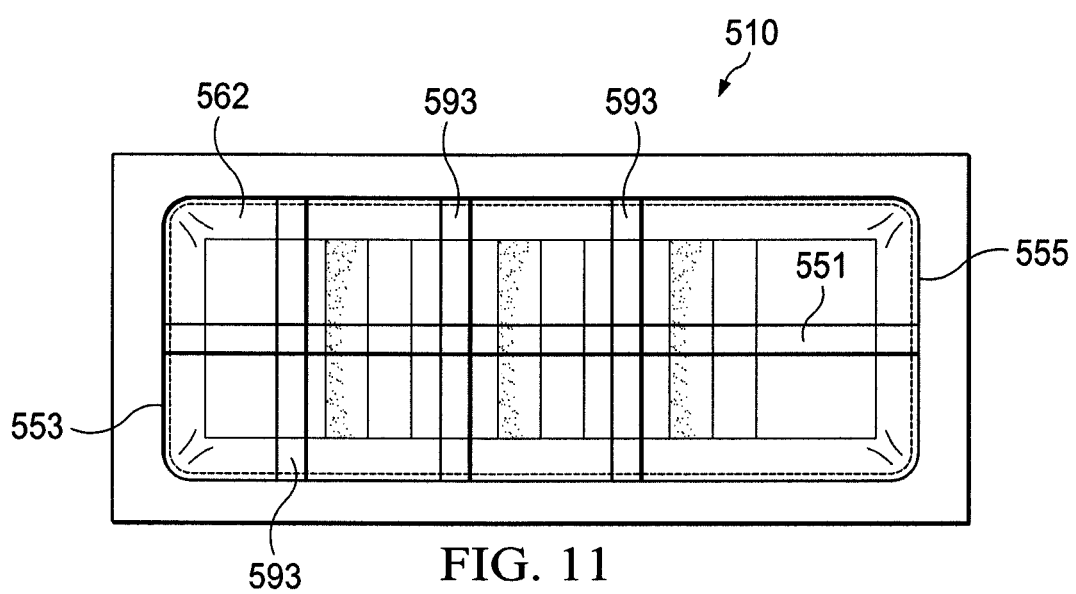
FIG. 11 is a schematic, plan view of an apparatus for applying reduced pressure to a tissue site according to an illustrative embodiment.

Referring now primarily to FIG. 11, an apparatus 510, or portion of a system, for applying reduced pressure to a tissue site is shown according to an illustrative embodiment. As with the drape 462 in FIGS. 8-10B, a drape 562 includes lateral folds 593 that accommodate longitudinal bending of a tissue site to which the apparatus 510 is applied. In contrast to the drape 462 in FIGS. 8-10B, the apparatus 510 also includes a longitudinal fold 551 that is able to accommodate lateral bending of the tissue site. Thus, the inclusion of lateral folds 593 and longitudinal fold 551 allows for the bending of the tissue site in multiple directions.

The longitudinal fold 551 may extend from one end 553 of the drape 562 to an opposing end 555 of the drape 562. Also, although the drape 562 is shown to include one longitudinal fold 551, the drape 562 may include any number of longitudinal folds 551.

Figure 12A:
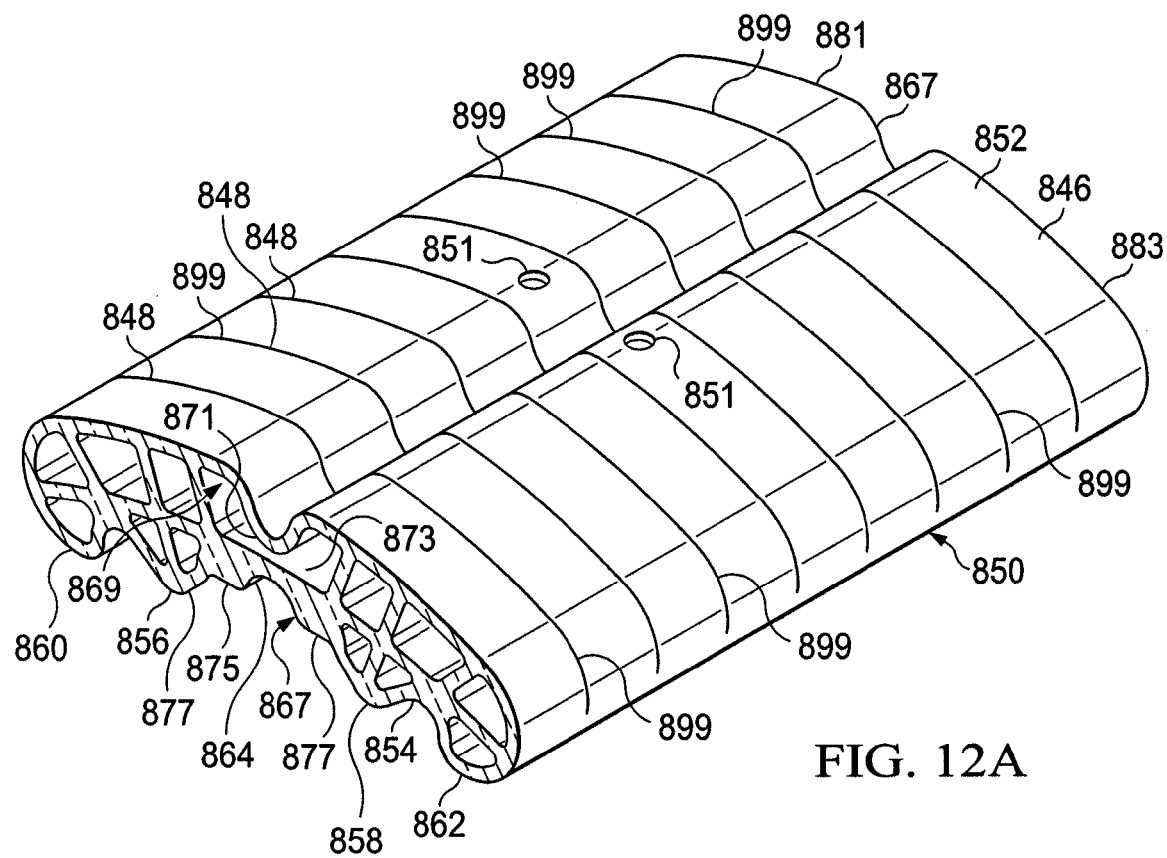
FIG. 12A is a schematic, perspective view of an illustrative embodiment of another flexible dressing bolster in an extended (straight) position.
Figure 12B:
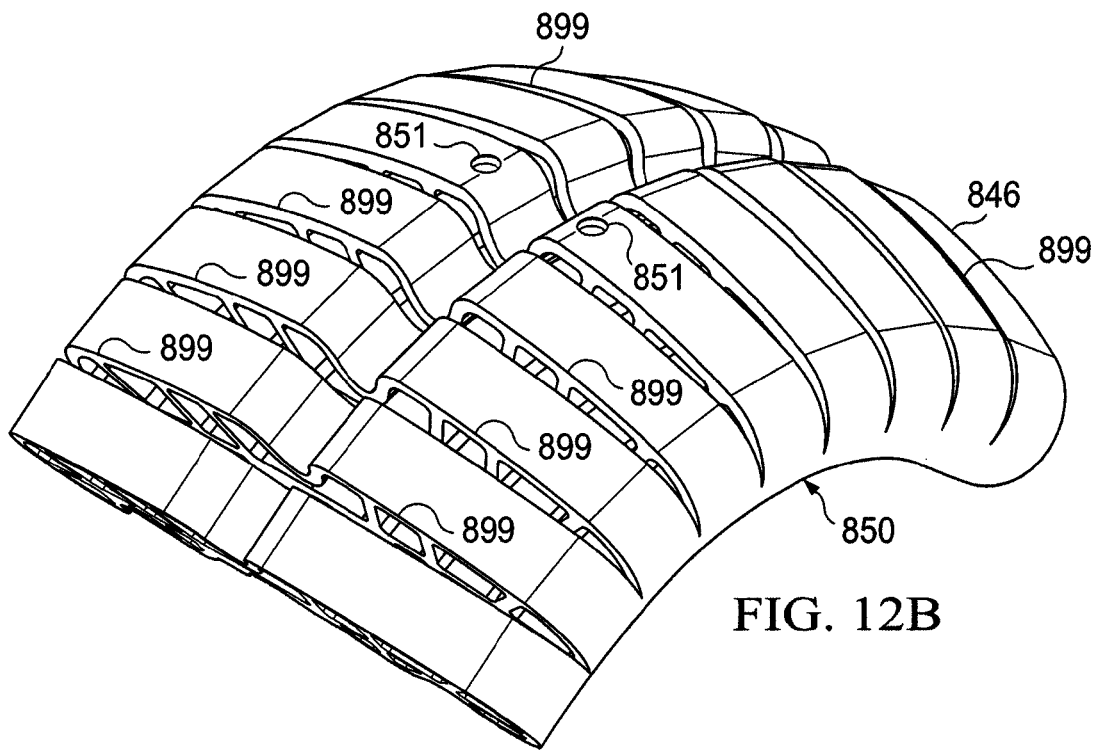
FIG. 12B is a schematic, perspective view of the flexible dressing bolster of FIG. 12A shown in a bent position.

Referring now primarily to FIGS. 12A and 12B, an illustrative embodiment of a flexible closing dressing bolster 846 for use with a system for treating a linear wound on a patient's joint is presented. "Linear wound" refers generally to a laceration or incision whether in a line or not. The flexible closing bolster 846 has a bolster body 850 having a first side 852 and a second, inward-facing (tissue-facing) side 854. The bolster body 850 is formed from a closing bolster material, i.e., a material from which the bolster body 850 is formed. The closing bolster material may be, for example, a silicone material. The bolster body 850 is formed with a plurality of flexion joints 848, which are formed with slots 899 that extend from the first side 852 into the bolster body 850.

The bolster body 850 is also formed with a first closing member 856 formed on the bolster body 850 on a first longitudinal side of a center wound area 864. As used here, the term "longitudinal" means substantially parallel to the center wound area 865 as shown—even if that dimension is shorter than the other orthogonal, in-plane dimension of the bolster body 850. A second closing member 858 is formed on the bolster body 850 on the second longitudinal side of the center wound area 864. Other closing members, e.g., members 860 and 862 may also be formed on the bolster body 850. The first closing member 856 and second closing member 858 are operable to develop an inward closing force when the flexible closing dressing bolster 846 is placed under reduced pressure. Apertures 851 may be formed on the first side 852 of the bolster body 850 to receive reduced pressure from a reduced-pressure source (not shown) and a plurality of apertures (not shown) may be formed on the second side 854 to allow the reduced pressure to fluidly communicate with a tissue site, e.g., a wound, in the center wound area 864.

As reduced pressure enters apertures 851, a central compartment 869 is evacuated and collapses such that a lower portion 871 of the central trough 867 contacts a shelf portion 873. In addition, reduced pressure enters into a treatment trough 875 through apertures in the shelf portion 873. The central compartment 871 has slots 899, but the central compartment is sealed by a drape. The treatment trough 875 includes oblique walls 877. The reduced pressure in the treatment trough 875 acts on the oblique walls 877 and pulls them towards each other. These actions cause the bolster body 850 to bend about the central trough 867 and causes the contact members on a first lateral side 881 and a second lateral side 883 to be urged towards each other. This results in a closing force.

The bolster body 850 may be made from a polymer and is preferably a soft polymer. The flexible closing dressing bolster 846 and the bolster body 850 may be made of a transparent material in order to allow the color of a linear wound to be viewed from a point external to the system or the flexible closing dressing bolster 846. For example, the bolster body 850 may be made of a medical grade silicone or other suitable material. The flexible closing dressing bolster 846 may be extruded, pour molded, injection molded, blow molded, or formed by other manufacturing techniques. The bolster material may serve to manifold, or distribute, the reduced pressure to the treatment site (e.g., a linear wound), provide a compressive force, and through the closing members provide an inward force—preferably a force that is substantially within the plane of the epidermis. In addition, the bolster material is preferably translucent or transparent, to an extent that light may pass through allowing one to view a wound through the flexible closing dressing bolster 846.

The central trough area 867 helps the bolster body 850 to flex in that region as a bending moment is developed under reduced pressure. The bending moment helps to press the closing members 856, 858, 860, and 862 into the patient's epidermis and may provide a directed force with both a downward force and inward force directed towards a central wound area.

Figure 13:
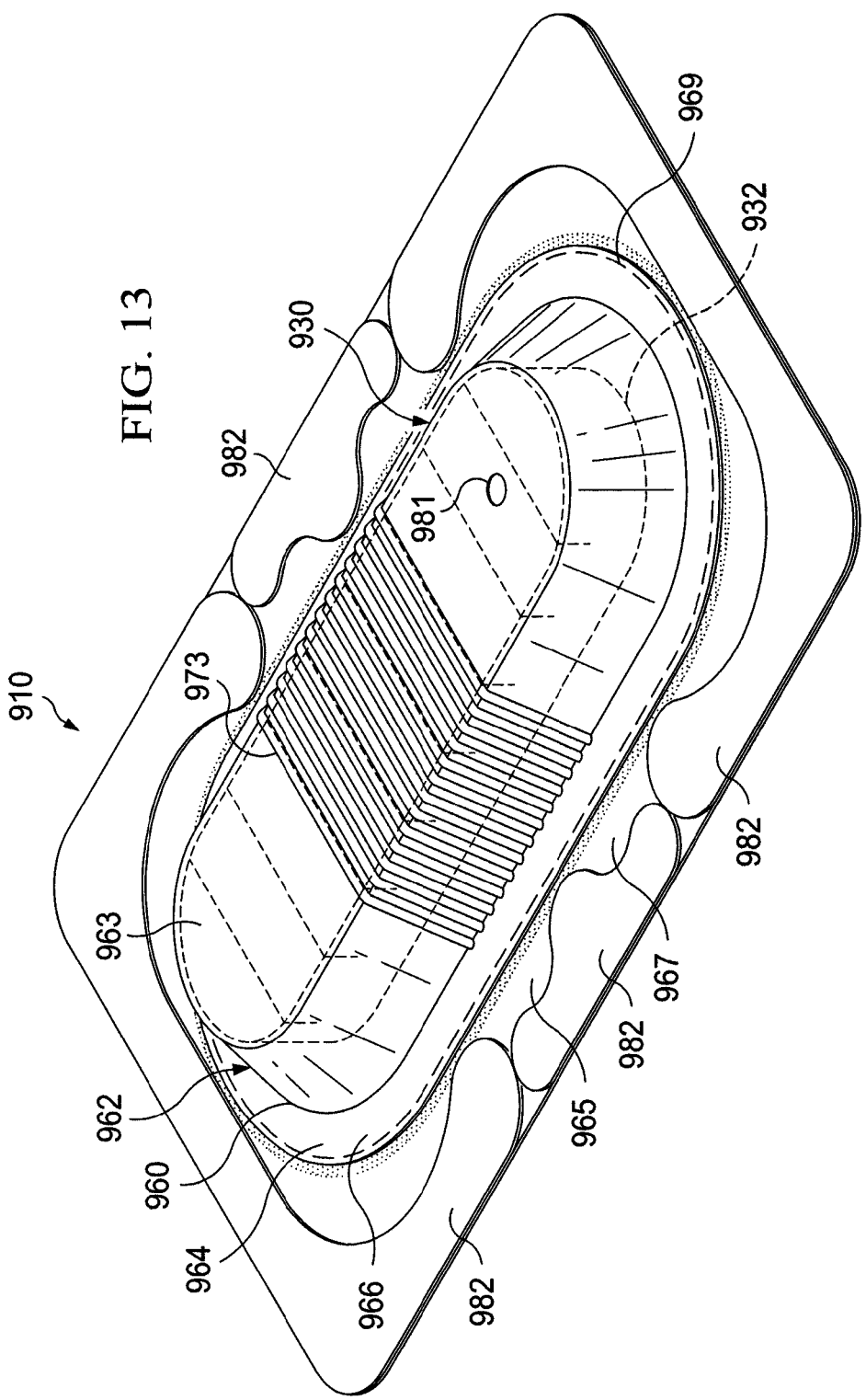
FIG. 13 is a schematic, perspective view of an illustrative embodiment of a dressing assembly suitable for use on a joint.
Figure 14:
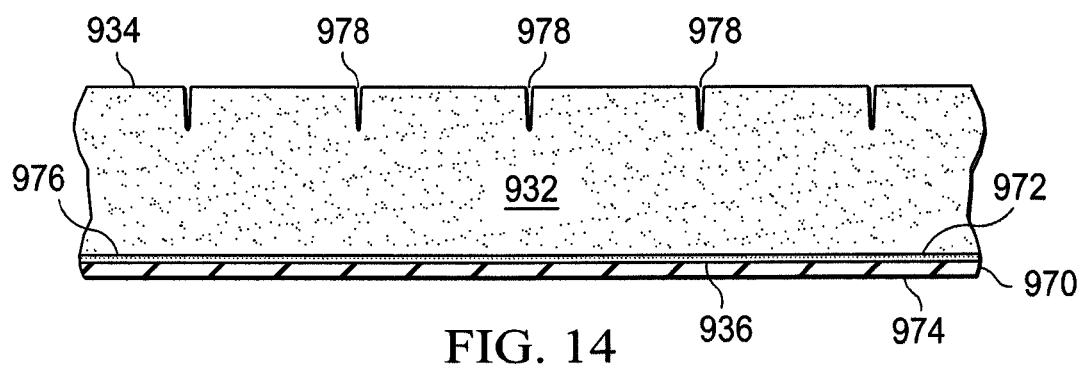
FIG. 14 is a cross sectional view of a portion of the dressing assembly of FIG. 13.
Figure 15:
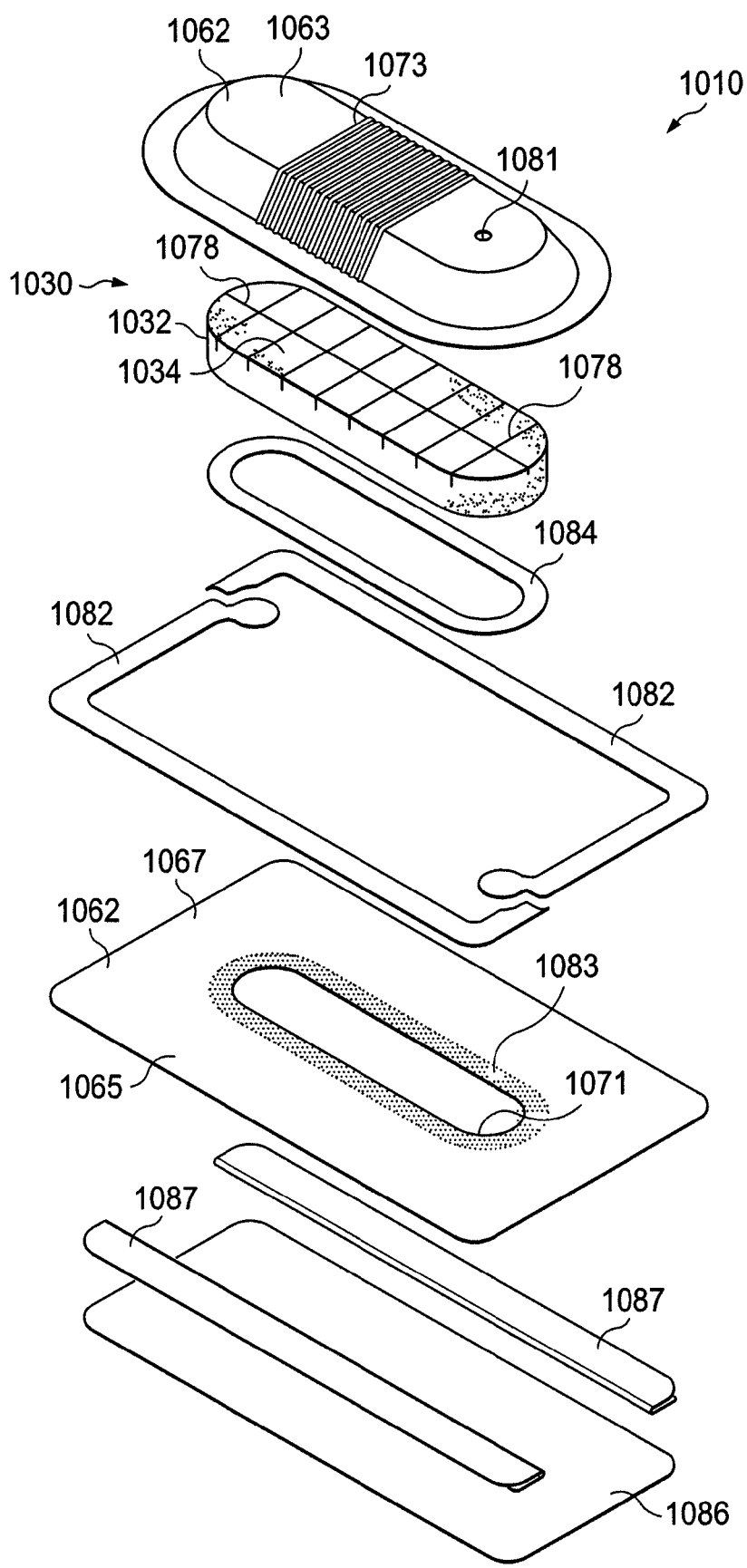
FIG. 15 is an exploded, schematic, perspective view of an illustrative embodiment of a dressing assembly.

Referring now to FIGS. 13-15, and initially to FIGS. 13-14, a portion of a system 910 for treating a linear wound, area wound, other wound, or graft is presented. The portion of the system 910 presented in FIG. 15 is in a pre-deployment state.

The system 910 includes a dressing assembly 930, which includes a flexible dressing bolster 932. The flexible dressing bolster, or shaped dressing bolster, 932 has a first side 934 and a second, inward-facing side 936. The flexible dressing bolster 932 may be formed from any bolster material as previously discussed with other embodiments. A comfort layer 970, which has a first side 972 and a second, inward-facing side 974, may be coupled, e.g., by a heat bond 976 or any other technique, to the second side 936 of the flexible dressing bolster 932.

The comfort layer 970 may be any material that helps prevent skin irritation and discomfort while allowing fluid transmission through the comfort layer 970. As one non-limiting example, a woven, elastic material may be used or a polyester knit textile substrate. As another non-limiting example, an InterDry™ textile material from Milliken Chemical of Spartanburg, S.C., may be used. The comfort layer 970 may include anti-microbial substances, such as silver.

The flexible dressing bolster 932 may include a plurality of flexibility notches 978, or recesses. The flexibility notches 978 may be lateral cuts in the flexible dressing bolster 932 as shown and may further include one or more longitudinal cuts or other cuts. The flexibility notches 978 enhance flexibility of the flexible dressing bolster 932. The enhanced flexibility may be particularly useful when the dressing assembly 930 is applied over a patient's joint or other area of movement.

A sealing subsystem 960 provides a fluid seal over the dressing assembly 930 and at least a portion of the patient's epidermis. The sealing subsystem 960 includes a drape 962, which may be formed with a first drape portion 963 and a second drape portion 965. The first drape portion 963 extends over the first side 934 of the flexible dressing bolster 932 and extends further to form a drape flange, or drape extension 964, which has a first side 966 and a second, inward-facing side (not explicitly shown). An aperture 981 is formed on a portion of the first drape 963. The aperture 981 is for allowing fluid communication with a reduced-pressure interface (e.g., reduced-pressure interface 92 in FIG. 1).

The second, inward-facing side of the drape extension 964 is placed on a first side 967 of the second drape portion 965 and coupled, such as by an adhesive, bond 969, other coupling technique or device, such as those previously mentioned. The first drape portion 963 may include a plurality of folds 973, or bellows. The folds 973 allow additional drape material to become available if needed. For example, if the dressing assembly 930 is used on a joint, when the joint is flexed, additional drape material may be necessary and the material will be provided from the folds 973. The second, inward-facing side of the second drape portion 965 may have an adhesive on a portion and may have a treatment area aperture (see by analogy treatment-area aperture 445 in FIG. 10A).

One or more release members 982 may be releasably coupled to the first side 967 of the second drape portion 965. Four release members 982 are shown in the illustrative embodiment of FIG. 13. The release members 982 provide stiffness and help during deployment of the dressing assembly 930. The release members 982 are typically either casting paper or a film held on the first side 967 of the second drape portion 965.

Referring now primarily to FIG. 15, an exploded perspective view of a portion of a system 1010 for treating tissue, e.g., subcutaneous tissue, a linear wound, area wound, other wound, or graft is presented. The portion of the system 1010 presented in FIG. 17 is shown in a pre-deployment state and in an exploded view. The system 1010 is analogous in most respects to the system 910 of FIGS. 13-14, and to indicate corresponding parts, the reference numerals have been indexed by 100 and may not be further mentioned. The system 1010 includes a dressing assembly 1030, which includes a flexible dressing bolster 1032. The flexible dressing bolster 1032 is the same as flexible dressing bolster 932, but the flexibility notches 1078 are both lateral and longitudinal.

The first side 1034 of the flexible dressing bolster 1032 is covered by a drape 1062, which may include a first drape portion 1063 and a second drape portion 1065. The first drape portion 1063 may include a drape-extension device 1073, such as folds, and an aperture 1081. The second drape portion 1065 is formed with a treatment area aperture 1071 that provides an opening for at least a portion of the flexible dressing bolster 1032 (or a comfort layer) to be directly against a patient's epidermis or treatment site. The second drape portion 1065 has first side 1067 and has an adhesive 1083 applied on a portion of the first side 1067. The adhesive 1083 is used primarily during manufacture to hold the flexible dressing bolster 1032 against the second drape portion 1065 during assembly and also used to help hold the flexible dressing bolster 1032 during use. Before applying the flexible dressing bolster 1032 against the adhesive 1083, the adhesive 1083 is covered by a center releaseable member 1084. Outboard of the adhesive 1083 on the first side 1067 are releaseable members 1082 that provides stiffness to the drape 1062 during deployment. In another embodiment, the drape-extension device 1073 may be a ridge of additional material that provides the ability to stretch over longer distances or more readily.

The second, inward-facing side (not explicitly shown but opposite side of the first side 1067) of the second drape portion 1065 may be covered with an adhesive. In the pre-deployment state, this adhesive is covered by a bottom release member 1086 and side release members 1087.

Once assembled, the portion of the system 1010 resembles the portion of the system 910 of FIG. 13. The use and design may vary, but in one illustrative embodiment, the portion of the system 1010 may be deployed as will be described. The bottom release liner 1086 is removed and the exposed adhesive on the second, inward-facing side of the second drape portion 1065 is placed against a portion of the patient's epidermis beginning at one end and may be placed over a linear wound. After smoothly applying the second drape portion 1065, the side release members 1087 are removed. The release members 1082 on the first side 1067 of the drape 1062 are removed. A reduced-pressure interface is coupled to the aperture 1082 in the first drape portion 1063. The center release member 1084 was already removed during manufacture.

In some situations, it may be desirable to have the flexible dressing bolster deliver the force as a lifting force. The density and thickness of the shaped dressing bolster 1032, which in this embodiment is foam, are variables for controlling lifting. As a substantially thick portion of a flexible dressing bolster 1032 experiences reduced pressure, the flexible dressing bolster 1032 contracts toward a central portion from all directions. The portion of the flexible dressing bolster 1032 near the patient's epidermis pulls away from the patient's epidermis since the central portion is above. This creates a radial, lifting force at least in a center area of the flexible dressing bolster 1032. In may be desirable to have a flexible dressing bolster 1032 formed from foam that has a density lighter than the density of the tissue, e.g., epidermis, to which the flexible dressing bolster is applied in order to more effectively realize the lifting effect.

According to another illustrative embodiment, a method of manufacturing a flexible, reduced-pressure dressing assembly for use on a moveable tissue site, e.g., a patient's joint, includes the steps of: forming a bolster body, which has a first side and a second side, from a bolster material; and forming a first plurality of bolster modules on the first side of the bolster body. Each bolster module has a bolster ridge. The method further includes the step of disposing a drape over the bolster ridges of the first side of the bolster body. The drape is formed from an elastomeric material and is operable to stretch longitudinally at least 80 percent.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A dressing assembly comprising:
    an intermediate drape having a treatment aperture;
    a bolster positioned over the treatment aperture and having a first side and a second, tissue facing, side;
    a comfort layer disposed over the tissue facing side of the bolster, at least a portion of the comfort layer configured to be in direct contact with the tissue site through the treatment aperture;
    a plurality of notches formed on the first side of the bolster; and
    a drape having a first portion and a second portion, the first portion disposed over the first side of the bolster and having an aperture and the second portion forming a drape extension which is coupled to the first portion.

2. The dressing assembly of claim 1, wherein the comfort layer is heat bonded to the bolster.

3. The dressing assembly of claim 1, wherein the comfort layer comprises a woven, elastic material or a polyester knit textile substrate.

4. The dressing assembly of claim 1, wherein the notches comprise lateral cuts in the bolster.

5. The dressing assembly of claim 1, wherein the notches comprise longitudinal cuts.

6. The dressing assembly of claim 1, wherein the notches comprise recesses.

7. The dressing assembly of claim 1, wherein the drape further comprises bellows disposed over the bolster.

8. The dressing assembly of claim 1, wherein the drape further comprises a plurality of folds disposed over the bolster.

9. The dressing assembly of claim 1, wherein the drape is formed from an elastomeric material and is operable to stretch longitudinally at least 80 percent of the drape's un-stretched length.

10. The dressing assembly of claim 1, further comprising an adhesive disposed on the intermediate drape around the treatment aperture, the adhesive bonding a portion of the bolster to the intermediate drape.

11. The dressing assembly of claim 10, further comprising at least one releasable member coupled to the intermediate drape outboard of the adhesive on a same side as the bolster.

12. The dressing assembly of claim 1, further comprising a bottom release member coupled to the intermediate drape.

13. The dressing assembly of claim 1, further comprising side release members coupled to the intermediate drape on a side opposite the bolster.

14. The dressing assembly of claim 1, wherein the bolster comprises:
    a top wall,
    a bottom wall coupled to the top wall in a spaced relationship, the bottom wall having a first lateral portion on one side of a center portion, and a second lateral portion on another side of the center portion,
    a first closing member formed on the first lateral portion, and
    a second closing member formed on the second lateral portion;

wherein the first closing member and second closing member are operable to develop a directed force when the bolster is placed under reduced pressured.

15. The dressing assembly of claim 1, wherein the bolster comprises a felted reticulated foam.

16. A system for applying reduced pressure to a tissue site, the system comprising:
a dressing assembly comprising:
an intermediate sealing member having a treatment aperture,
a manifold positioned over the treatment aperture and having a first side and a second, tissue facing, side,
a wound-contact layer disposed over the tissue facing side of the manifold, at least a portion of the wound-contact layer configured to be in direct contact with the tissue site through the treatment aperture,
a plurality of notches formed on the first side of the manifold, and
a sealing member having a first portion and a second portion, the first portion disposed over the first side of the manifold and having an aperture and the second portion forming a sealing member extension which is coupled to the first portion; and
a reduced-pressure source configured to be fluidly coupled to the dressing assembly.

17. The system of claim 16, wherein the wound-contact layer is heat bonded to the manifold.

18. The system of claim 16, wherein the notches comprise lateral cuts in the manifold.

19. The system of claim 16, wherein the notches comprise longitudinal cuts.

20. The system of claim 16, wherein the notches comprise recesses.

21. The system of claim 16, wherein the sealing member further comprises bellows disposed over the manifold.

22. The system of claim 16, wherein the sealing member further comprises a plurality of folds disposed over the manifold.

23. The system of claim 16, further comprising an adhesive disposed on the intermediate sealing member around the treatment aperture, the adhesive bonding a portion of the manifold to the intermediate sealing member.

24. The system of claim 16, wherein the manifold comprises:
a top wall,
a bottom wall coupled to the top wall in a spaced relationship, the bottom wall having a first lateral portion on one side of a center portion, and a second lateral portion on another side of the center portion,
a first closing member formed on the first lateral portion, and
a second closing member formed on the second lateral portion;
wherein the first closing member and second closing member are operable to develop a directed force when the manifold is placed under reduced pressured.

* * * * *